United States Patent [19]

Uchiyama et al.

[11] Patent Number: 4,984,575

[45] Date of Patent: Jan. 15, 1991

[54] THERAPEUTICAL APPARATUS OF EXTRACORPOREAL TYPE

[75] Inventors: Naoki Uchiyama; Takashi Tsukaya; Kouichiro Ishihara; Sakae Takehana; Tetsumaru Kubota; Syuichi Takayama; Akira Taniguchi; Nobuhiko Watanabe; Naomi Sekino; Hiroki Hibino; Masaaki Hayashi, all of Hachioji, Japan

[73] Assignee: Olympus Optical Co., Ltd., Japan

[21] Appl. No.: 182,785

[22] Filed: Apr. 18, 1988

[30] Foreign Application Priority Data

| Apr. 16, 1987 | [JP] | Japan | 62-94870 |
| Apr. 17, 1987 | [JP] | Japan | 62-94583 |
| Apr. 25, 1987 | [JP] | Japan | 62-102809 |
| Apr. 27, 1987 | [JP] | Japan | 62-102071 |
| Apr. 28, 1987 | [JP] | Japan | 62-105637 |
| May 20, 1987 | [JP] | Japan | 62-124838 |
| Jun. 18, 1987 | [JP] | Japan | 62-152777 |
| Jun. 19, 1987 | [JP] | Japan | 62-153163 |
| Jun. 22, 1987 | [JP] | Japan | 62-155749 |

[51] Int. Cl.$^5$ .......................................... A61B 17/22
[52] U.S. Cl. ............................ 128/660.03; 128/24 EL
[58] Field of Search ............... 128/328, 24 A, 24 EL, 128/660.03; 606/127–128

[56] References Cited

U.S. PATENT DOCUMENTS

| 4,526,168 | 7/1985 | Hassler et al. | |
| 4,617,931 | 10/1986 | Dory | 128/328 S |
| 4,669,483 | 6/1987 | Hepp et al. | 128/328 S |
| 4,763,652 | 8/1988 | Brisson et al. | 128/24 EL |
| 4,771,787 | 9/1988 | Wurster et al. | 128/24 EL |
| 4,796,613 | 1/1989 | Heumann et al. | 128/24 EL |
| 4,803,995 | 2/1989 | Ishida et al. | 128/328 S |
| 4,821,729 | 4/1989 | Makofski et al. | 128/24 EL |
| 4,836,191 | 6/1989 | Noske et al. | 128/24 EL |

OTHER PUBLICATIONS

Martin et al., Ultrasound Stone Localization for Extra-Corporeal Shock Wave Lithotripsy, British Journal of Urology, 1986, pp. 349–352.

Primary Examiner—Lee S. Cohen
Assistant Examiner—John D. Zele
Attorney, Agent, or Firm—Ostrolenk, Faber, Gerb & Soffen

[57] ABSTRACT

A therapeutical apparatus includes a measuring apparatus including a probe which generates an X-ray or ultrasonic wave in order to detect the location of a target to be treated such as calculi situated within the kidney, liver, biliary ducts. A therapeutical energy generator generates a shock wave of sufficient energy for purpose of therapy externally of the physical body and focusses it upon the target. Structure is provided for causing a displacement of the generator and the measuring apparatus around the surface of a patient. Structure is provided to activate the generator.

2 Claims, 27 Drawing Sheets

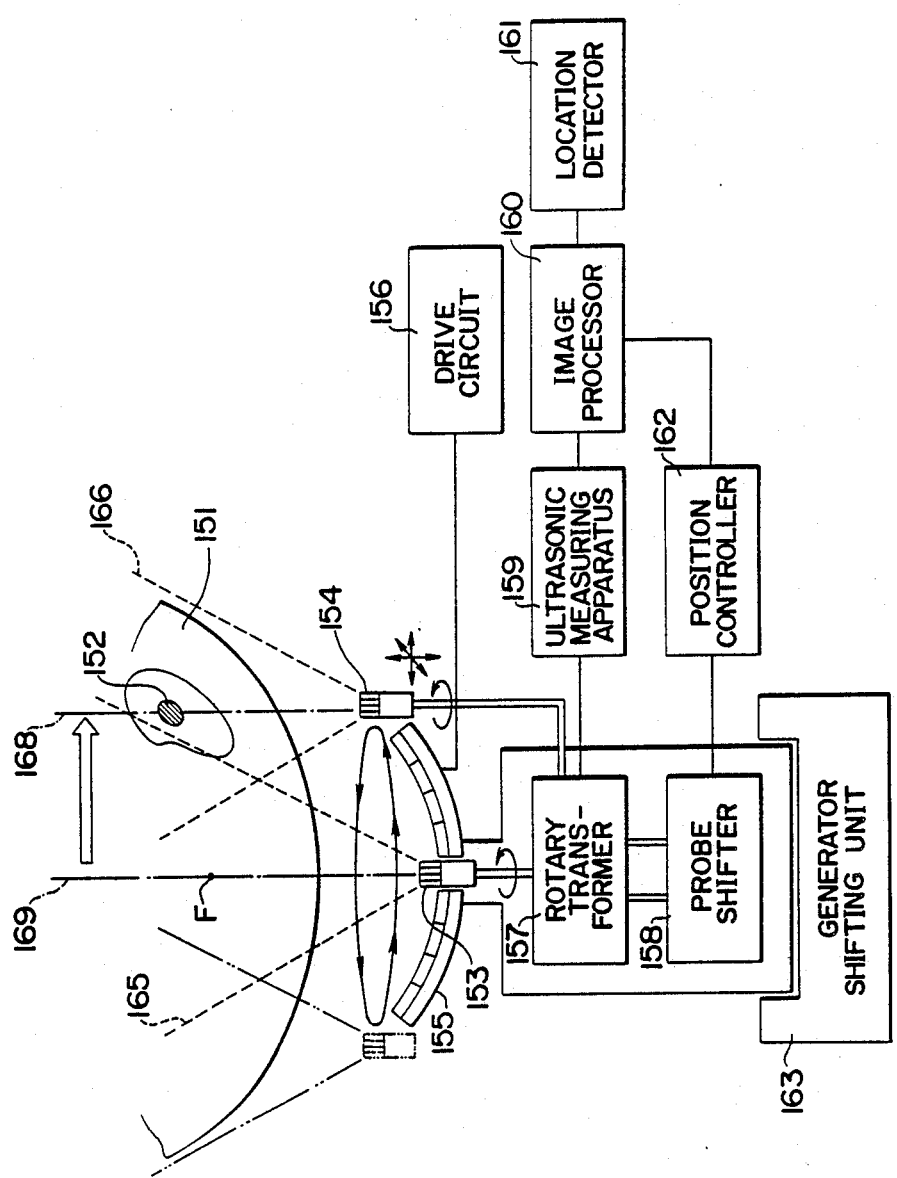

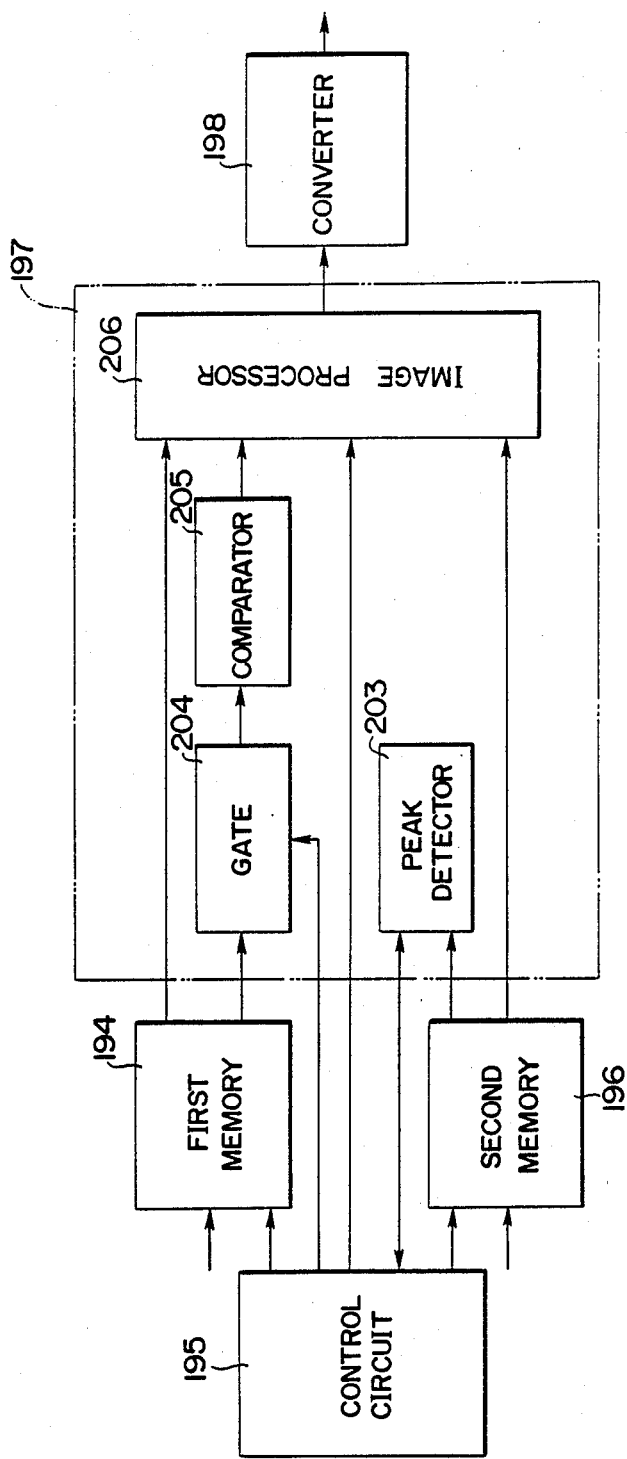
F I G. 38

THERAPEUTICAL APPARATUS OF EXTRACORPOREAL TYPE

BACKGROUND OF THE INVENTION

1. Field of the Invention

The present invention relates to a therapeutical apparatus of extracorporeal type, and more particularly, to a therapeutical apparatus of extracorporeal type in which an object to be treated (such as a calculus formed within a physical body of a patient) is detected by a measuring apparatus, and therapeutic shock wave energy which is generated externally of the physical body is focussed upon the object to fracture it, and specifically, to an ultrasonic therapeutical apparatus which focuses an ultrasonic shock wave from a source located externally of the physical body upon the object to be treated for the purpose of fracturing the same.

2. Prior Art

An arrangement which utilizes an X-ray or ultrasonic measuring apparatus to detect the presence of a calculus formed in a bile duct or kidney, and which also utilizes therapeutical energy in the form of a shock wave which is produced, as by voltage discharge or ultrasonic vibration, externally of the physical body of a patient and is focussed upon the calculus to fracture it, is disclosed in U.S. Pat. No. 4,617,931. As disclosed in this patent, a probe with piezoelectric elements disposed in an array in a mosaic pattern along a quadratic surface is brought into contact with a patient's back via a water bag filled with an ultrasonic wave transmitting medium such as water interposed therebetween to focus an ultrasonic shock wave from the piezoelectric elements upon a calculus, as formed within a kidney, to fracture it. As disclosed in Japanese Laid-Open patent applications No. 31,140/1988 and No. 45,747/1986, an ultrasonic probe may move across an extensive area and focus an ultrasonic wave of increased intensity upon a calculus once it is located. Japanese Laid-Open patent application No. 37,149/1986 discloses a measuring apparatus including a detection system which determines positions in two directions. The present applicant has also proposed an arrangement which permits displacement of the ultrasonic probe in a direction perpendicular to the scan direction, as disclosed in Japanese patent application No. 282,979/1986. U.S. Pat. No. 4,526,168 discloses a technique for focussing an ultrasonic wave upon a calculus by changing the timing and phases with which a plurality of piezoelectric elements are driven. In the ultrasonic therapeutical apparatus disclosed in U.S. Pat. No. 4,617,931, the ultrasonic probe is located only at the center of an ultrasonic wave generator which provides an ultrasonic wave of an increased intensity, resulting in a limited scanning field over which an observation is possible. However, such an arrangement may fail to locate a calculus. When displacement of the probe in a direction perpendicular to the scan direction is enabled as disclosed in Japanese patent application No. 282,979/1986, tracking the movement of the calculus is possible, but it is still difficult to locate the calculus before the therapy is conducted. A manual focussing operation results in a low hit rate of the ultrasonic wave whenever the calculus happens to move as a result of breathing.

The ultrasonic therapeutical apparatus disclosed in Japanese Laid-Open patent application No. 31,140/1986 enables the extent of observation to be increased, but involves a combination with a patient suspension system with the patient suspended in a bath in a water vessel, thus disadvantageously requiring a very bulky arrangement. The ultrasonic therapeutical apparatus disclosed in Japanese Laid-Open patent application No. 37,149/1986 uses X-ray in its detector, which may be hazardous to the patient. In addition, where a pair of ultrasonic probes are employed, they are located such that each scan plane passes through the focus of a reflector of the shock wave and such that their axes are perpendicular to each other. This limits the extent of observation which is available, and thus still leaves much to be improved.

The apparatus disclosed in U.S. Pat. No. 4,617,931 includes means for focussing a shock wave on a calculus. Specifically, an ultrasonic wave or X-ray is employed to detect the spatial location of a calculus within the physical body of a patient, as illustrated in FIG. 46, where the focal point of the shock wave is indicated by a marker on an image 300 which is obtained by ultrasonic or X-ray tomography. The positioning is achieved by bringing an image 302 of a calculus into alignment with the marker. Thus, the position of a focus F is indicated as shown at 304 on a display 303, and the means for generating a shock wave is moved so that the image 302 of the calculus is aligned with the position of the focus F. However, such technique only indicates the focal point of the display.

Accordingly, where organs such as lungs, intestines or bones, which are sensitive to the shock wave, are located around the calculus when the latter is to be fractured, there arises a significant problem inasmuch as such organ may be damaged or otherwise adversely influenced by the shock wave.

Another form of therapeutical apparatus of extracorporeal type is disclosed in Japanese patent application No. 282,980/1986 (see FIGS. 44 and 45). The apparatus includes ultrasonic measuring means 311 (location detecting means) which detects the location of a calculus within the physical body, positioning signal generating means 312, focus shifting means 313 and shock wave generating means 314 which generates a shock wave used to fracture a calculus.

The ultrasonic measuring means 311 includes an ultrasonic measuring unit 317 which radiates an ultrasonic wave toward a patient 315 to detect the location of a calculus 316, and a display unit 318 which receives a detection signal to indicate the location of the calculus on a CRT screen.

The positioning signal generating means 312 includes a single generator 320 which fixes a marker on a given point on the screen of the display unit 318 and produces a signal which is delivered to focus shifting means 313 which is effective to bring the focus of the fracturing shock wave into alignment with the marker. The generator 320 is effective to process the image of the detected calculus so that an operator (such as a surgeon) can recognize the size or the number of calculus or calculi displayed and to indicate a most effective signal on the screen as by a light pen to indicate the sequence in which the calculi are to be fractured in order of decreasing size, or to indicate a particular region of a coral calculus where the fracture is to be initiated or to change the focal point of the shock wave in response to the location and size of the calculus which is performed periodically during the fracturing process because of a displacement of the calculus. The generator stores such signals, and delivers them to a drive unit 319 which shifts the shock wave generator during the fracturing process.

The focus shifting means 319 or the drive unit which shifts the shock wave generator operates to drive both a water bag 321 and a shock wave generator 322 by means of a numerically controlled robot in accordance with the positioning signal. The shock wave generator 322 includes a plurality of ultrasonic vibrators or piezoelectric elements 323 which are applied to and secured to the front surface of a mounting plate 324, which is formed as a spherical surface, in a mosaic pattern. The front surface of the piezoelectric elements which emit the shock wave is directed toward the patient 315. The water bag 321 includes an ultrasonic wave transmitting medium and means for injecting liquid medium and controlling the pressure of the medium.

The water bag is interposed between the shock wave generator 322 and the patient 315. The shock wave transmitting liquid (such as water) fills the bag 321.

The shock wave generating means 314 includes a known ultrasonic pulse voltage generator for driving the piezoelectric elements 323.

FIG. 45 indicates the sequence of operation performed by the apparatus mentioned above. Initially, the location of the calculus within the physical body of a patient is determined by the measuring means 311. The positioning signal generating means 312 analyses the condition of the calculus which is detected by the measuring means. An operator (such as a surgeon) selects an optimum procedure to treat the calculus depending on the kind thereof. In response thereto, a positioning signal (which determines the sequence of treatment) is stored. The focus shifting means 313 is activated in accordance with the positioning signal to drive the water bag 321 and the shock wave generator 322 so that the shock wave is focussed upon the calculus. Subsequently, a shock wave is generated in response to the shock wave generating means 314 to fracture the calculus. After a given number of shock waves have been generated, the procedure is temporarily stopped, and the size of the remaining calculus or the focal point of the shock wave is determined again, and the above operation is repeated until the calculus is completely fractured.

However, in the therapeutical apparatus of extracorporeal type as mentioned above, the use of the ultrasonic wave for observing the location of a calculus and for aiming fails to provide a tomographic image of good quality because of the spacing between the apparatus and the patient. This makes it difficult to aim the apparatus.

In addition, in the apparatus described above, the entire shock wave generator has been moved in order to bring the focal point of the shock wave into alignment with the calculus. However, because the shock wave generator (including the water bag) is of an increased weight, an extensive unit is required for such movement and the apparatus lacks speed.

On the other hand, a calculus or tumor which is to be treated by such an apparatus tends to move in response to breathing or movement of blood vessel, and thus may be displaced from the focal point of the ultrasonic beam. In such instance, the focal point of the ultrasonic beam must be aligned with a region to be treated to avoid wasteful generation of an ultrasonic wave. This increases the length of time required for the therapy and also jeopardizes normal tissues. Movement caused by breathing may be rapid enough to prevent automatic tracking of the focal point of the ultrasonic beam on the moving calculus since the water bag itself has a given magnitude.

Almost all apparatus of the kind described utilize a devoted bed on which a patient is positioned in a supine posture. The bed includes a table section supporting an upper region of a patient including his shoulder and head and another table section supporting a lower section extending from the waist to the feet, leaving a free space between the breast and the abdomen. A patient is laid in a supine posture on the bed, and the measuring apparatus as well as a unit for generating therapeutical energy are brought close to or into abutment against the patient to perform the treatment. Accordingly, the patient has a small degree of freedom during the therapy, which restricts the space requirement for the measuring apparatus and the energy generating apparatus. Specifically, with an X-ray measuring apparatus, it is only possible to cause the X-ray to transmit through the physical body of a patient. With an ultrasonic measuring apparatus, it is only possible to move the ultrasonic vibrator along the surface of the physical body.

There has been no capability to provide an efficient, fine adjustment of the angle with which the X-ray transmits or the angle at which the ultrasonic wave is emitted. It has been impossible to locate a shock wave generator at an angle which avoids the lung when treating a biliary calculus or to adjust the angle at which the shock wave is emitted to an efficient angle. It has only been possible to guide the shock wave generator along the physical body of a patient.

Usually, a supine posture is chosen for therapy of a biliary calculus while either a supine or prone posture is chosen for treating a renal calculus, and it is unfavorable that a posture used for the therapy be restricted by a devoted bed.

Hospitals usually have an X-ray apparatus and an ultrasonic diagnostic apparatus, and therefore it is uneconomical for the hospital to purchase a separate extracorporeal therapeutical apparatus with a devoted bed. It is desirable that a therapeutical apparatus of extracorporeal type be provided which uses a common bed which allows a free choice of either supine or prone posture.

Thus, an ordinary hospital is usually provided with an X-ray unit or ultrasonic diagnostic apparatus which may be used as the measuring apparatus mentioned above as well as associated patient beds. If an extracorporeal therapeutical apparatus as mentioned above must be provided anew, an increased demand in space requirement and additional cost result.

SUMMARY OF THE INVENTION

It is an object of the present invention to provide a therapeutical apparatus of extracorporeal type which permits a choice of therapy postures and which improves economy and which is capable of adjusting an angle with which a measuring apparatus makes an observation as well as an angle with which energy from a therapeutical energy generator is emitted or directed.

It is a second object of the invention to provide a therapeutical apparatus of extracorporeal type which requires less space and reduces cost while utilizing an ultrasonic diagnostic apparatus or X-ray unit which is already available in the hospital.

It is a third object of the invention to eliminate disadvantages of the prior art, by providing an ultrasonic therapeutical apparatus having enhanced measurement capabilities while facilitating the location of a calculus before therapy and also enabling an accurate tracking of the calculus for efficient therapy.

It is a fourth object of the invention to provide a therapeutical apparatus of extracorporeal type which is capable of detecting movement of a calculus to bring a focus into alignment with the calculus which has quickly moved, thus providing efficient and dependable therapy.

It is a fifth object of the invention to provide a therapeutical apparatus of extracorporeal type which is capable of reliably bringing the focal point of a shock wave into alignment with a recognized calculus in an accurate manner while avoiding adverse influence upon other organs, thus further improving the fracture efficiency and reducing the length of time required for the therapy while avoiding any pains to the patient.

It is a sixth object of the invention to provide an ultrasonic probe having a simplified construction and exhibiting an increased efficiency. In accordance with the invention, the patient may assume any posture during therapy. The angle at which an observation is made as well as the angle at which the shock wave used for the therapy is emitted can be accurately adjusted to achieve a most efficient operation. The apparatus of the invention may be efficiently used in combination with any other instrument such as an X-ray unit. This avoids unnecessary expenses and reduces space requirements while improving the degree of freedom and economy.

In accordance with the invention, an ultrasonic shock wave is radiated in recognition of the location within a specified area (an area of interest—AOI) where a calculus exists, thus eliminating a wasteful emission of an ultrasonic shock wave to provide a further enhanced therapy efficiency.

In accordance with the invention, an ultrasonic probe allows an increased coverage for observation, facilitating the location of a calculus before it is treated. In this manner, any resort to a separate ultrasonic observation unit as has been done conventionally is avoided. The locating and the automatic tracking of a calculus enable the length of time required for the therapy to be reduced and any pain caused to the patient to be diminished, because an efficient treatment is achieved.

In accordance with the invention, the focal point of an ultrasonic shock wave may be brought into alignment with any object being treated which may move rapidly as a result of breathing, by merely choosing ultrasonic vibrators which are to be driven while maintaining a shock wave generator at a fixed position. The focal point is brought into alignment with the object by an electronic technique which utilizes a CPU to drive a drive circuit, and hence the arrangement is compact in construction and efficient in achieving the therapy of an object such as a calculus.

Additionally, if a calculus or tumor changes its position because of the patient's breathing, the ultrasonic wave may be maintained focussed on the object being treated. This improves the efficiency of the therapy and enhances the safety of the therapy by avoiding concentration of an ultrasonic wave upon areas which are unrelated to treatment. This is achieved by feeding a digital signal representing the location of a calculus or tumor detected by the ultrasonic probe to a CPU, which then automatically focuses the ultrasonic wave on an area to be treated, thus avoiding manual intervention and allowing an automatic tracking.

Additionally, in accordance with the invention, an image representing a spatial location of a focus within the patient may be obtained by driving ultrasonic vibrators. Data representing the distribution of the intensity of the ultrasonic wave which is previously calculated is superimposed upon the image to provide a color display, whereby the location of the calculus may be readily and reliably positioned to a point where the intensity of the shock wave is at its maximum. This also allows a decision to see if any organ such as a lung, intestine or bones which are sensitive to the shock wave is located within a region where the intensity of the shock wave is significant. In this manner, any damage to such organ may be avoided by changing the posture of the patient or by moving the shock wave generator.

Other features and advantages of the present invention will become apparent from the following description of the invention, with reference to the accompanying drawings.

BRIEF DESCRIPTION OF THE DRAWINGS

FIG. 26A being a cross sectional view of the relationship between an acoustical prism and a focal point.

FIG. 27 is a schematic illustration of an apparatus according to a fourteenth embodiment of the invention;

FIG. 38 is a block diagram of another form of display means;

DETAILED DESCRIPTION OF THE PREFERRED EMBODIMENTS

Figure 1:
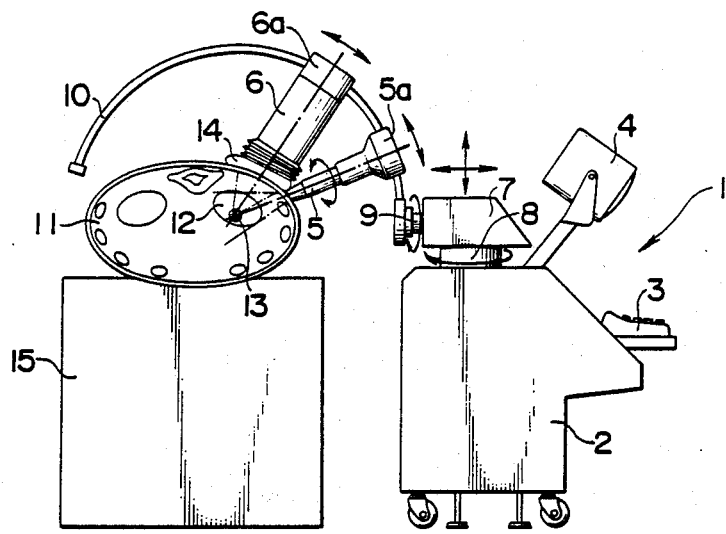
FIG. 1 is a side elevation of an apparatus according to a first embodiment of the invention.

Referring to the drawings, the invention will now be described with reference to several embodiments thereof. In the description to follow, a therapeutical apparatus of extracorporeal type is constructed as a calculus fracture apparatus, but it should be understood that the invention is not limited in its application to the fracture of a calculus.

The apparatus 1 of FIG. 1 includes a movable body 2 on which an operating keyboard 3 and a monitor display 4 are installed. An operating head 7 is also carried. The head 7 guides a measuring apparatus 5 and a therapeutical energy generator 6 to a desired angular position.

The head 7 is mounted on the top end of a rotatable shaft 8 which is vertically supported within the body 2. The shaft 8 can be elevated up and down to permit vertical movement of the head 7, which is also movable toward and away from a patient 11 by a mechanism, not shown. The head 7 carries a support shaft 9 which projects horizontally and forwardly, with a guide arm 10 mounted on the free end of the support shaft 9. The measuring apparatus 5 is slidably mounted on the arm 10 by a movable mount 5a, and the energy generator 6 is also slidably mounted on the arm 10 by a movable mount 6a. The guide arm 10 is arcuate or semicircular in the present embodiment so that both the measuring apparatus 5 and the generator 6 may be moved around one-half the circumference of the patient 11. The support shaft 9 is also rotatable around its axis, whereby the guide arm 10 is rotatable through 360° around an extension of the axis of the support shaft 9.

The measuring apparatus 5 (mounted on the movable mount 5a) includes an ultrasonic vibrator which performs a sector scan, for example, radiating an ultrasonic wave toward the patient 11 to detect the location of a calculus 13 which may be located within a kidney 12 of the patient. The detected renal calculus 13 is displayed on the screen of the monitor display 4 (which may include a cathode ray tube).

The therapeutical energy generator 6 (mounted on the movable mount 6a) includes a high tension discharge type source for generating shock wave energy. The source is focussed upon the renal calculus 13 within the patient 11, through an interposed water bag 14 (such as GOATEX (trademark)) which is filled with a shock wave transmitting medium (such as water) for fracturing the calculus 13.

Figure 2:
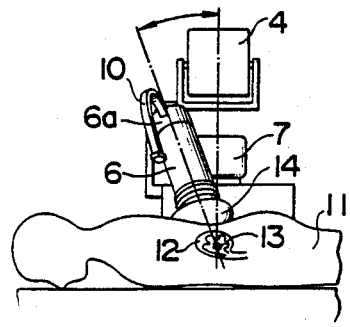
FIGS. 2 and 3 are a fragmentary rear view and a side elevation, illustrating manners of operating the apparatus illustrated in FIG. 1.
Figure 3:
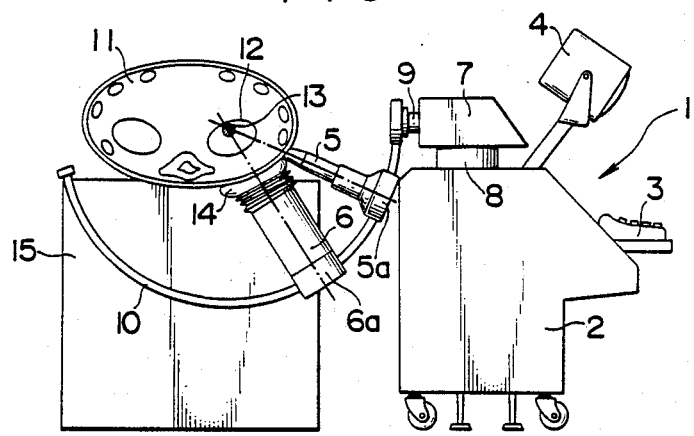

In operation, the patient 11 usually lies on an ordinary bed 15 in prone posture, and the body 2 is moved close to the patient. By adjusting the operating head 7 back and forth and up and down, the guide arm 10 is brought in spaced, opposing relationship with the circumference of the patient 11 to facilitate detection and fracture of the calculus by bringing the measuring apparatus 5 and the energy generator 6 close to or in abutment against the surface of the patient. As illustrated in FIG. 2, the support shaft 9 may be rotated around its axis to bring the guide arm 10 to an inclined position with respect to the surface of the patient so that the generator 6 may be brought to an angular position to maximize fracture efficiency or where the location of a lung or the like may be avoided from the path of the shock wave energy.

Where the patient 11 lies on the bed 15 in supine posture as illustrated in FIG. 2, the support shaft 9 may be rotated through 180° to position the guide arm 10 in the space below the bed 15, whereby the measuring apparatus 5 and the generator 6 are brought close to or into abutment against the patient 11 from the underside thereof for therapy.

Figure 4:
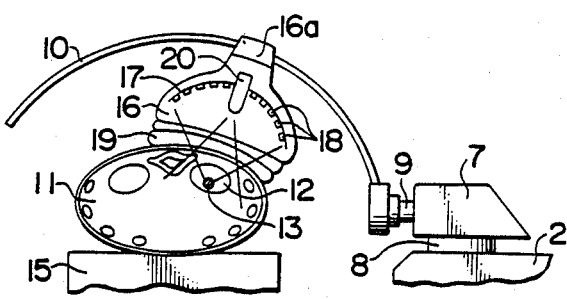
FIG. 4 is a schematic view of a therapeutical apparatus according to a second embodiment of the invention.

FIG. 4 is a schematic illustration of an apparatus according to a second embodiment of the invention. This apparatus differs from the first embodiment in that the energy generator 6 includes an ultrasonic shock wave generator 16. Specifically, the generator 16 includes a mounting plate 17 in the form of a spherical shell. A multiplicity of ultrasonic vibrators 18, formed by piezoelectric elements, are secured in a mosaic pattern on the internal surface of the shell so that the front surface of each element (on which a shock wave is generated) faces the patient 11. A water bag 19 of a material such as GOATEX (trademark) which includes liquid injection means and pressure control means is interposed between the generator and the patient 11. The bag 19 is filled with a shock wave transmitting liquid such as water. An ultrasonic measuring apparatus 20 which is adapted for a linear scan or a sector scan is mounted centrally on the mounting plate 17.

The ultrasonic energy generator 16 is movably mounted on the guide arm 10 by a movable mount 16a. In other respects, the arrangement is similar to the first embodiment, and this embodiment operates similarly and with a similar effect as in the first embodiment.

Figure 5:
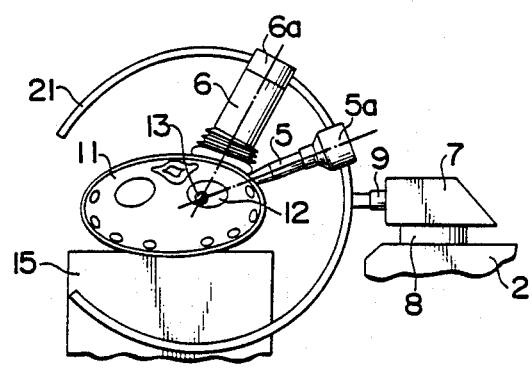
FIG. 5 is a side elevation of another form of guide arm.

In FIG. 5, the guide arm 10 of the first embodiment is replaced by a C-ring shaped guide arm 21 on which the measuring apparatus 5 and the therapeutical energy generator 6 may be movably mounted. This facilitates changing the posture of the patient. This permits utilization of an X-ray unit having a C-shaped guide arm as the measuring apparatus associated with the therapeutical apparatus of the invention.

Figure 6:
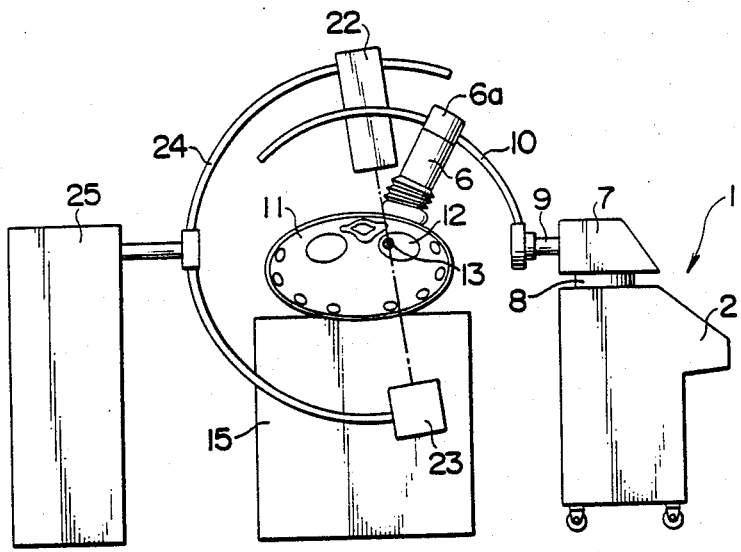
FIG. 6 is a side elevation of an apparatus according to the invention in combination with an X-ray unit.

Specifically, as illustrated in FIG. 6, an X-ray unit 25 carries a C-shaped guide arm 24 on which an X-ray emitter 22 and an image intensifier 23 (which is an X-ray receptor and includes photomultipliers) are mounted in opposing relationship. The unit 25 may be disposed along one side of the patient 11 lying on the bed 15 while the therapeutical apparatus 1 (including either the therapeutical energy generator 6 or 16) mounted on the guide arm 10 may be disposed on the other side. In this manner, the location of the calculus 13 may be detected by the X-ray observation unit 25, and then the therapeutical apparatus 1 may be activated to fracture the calculus 13.

Figure 7:
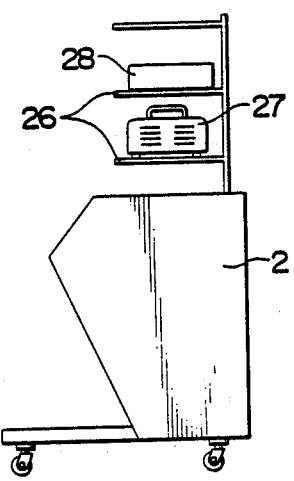
FIG. 7 is a side elevation of another form of the therapeutical apparatus.

The therapeutical apparatus of the invention may be used in combination with an endoscope. As illustrated in FIG. 7, the body 2 of the therapeutical apparatus may be provided with shelves 26 on which a light source unit 27 for the endoscope and a treatment tool 28 may be conveniently located.

Figure 8:
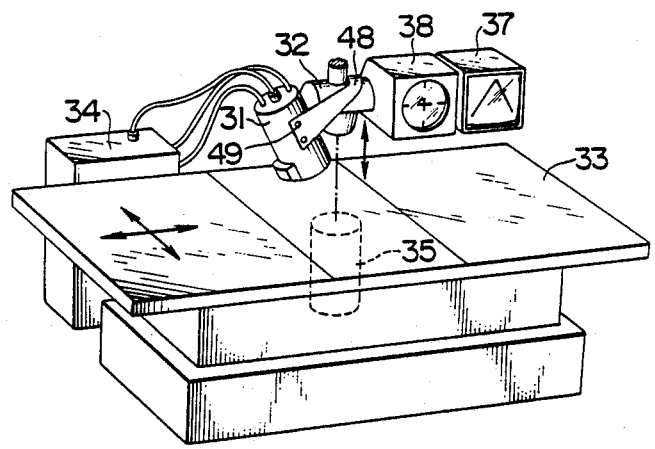
FIG. 8 is a perspective view of an apparatus according to a third embodiment of the invention.
Figure 9:
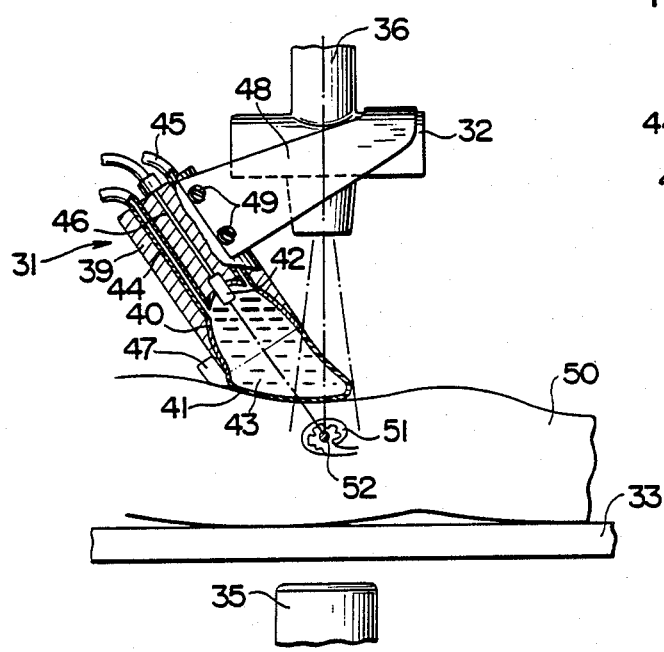
FIG. 9 is a fragmentary, enlarged, longitudinal section illustrating one manner of use of the apparatus illustrated in FIG. 8.
Figure 10:
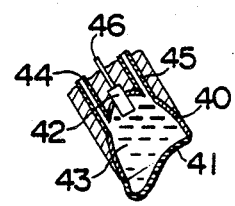
FIG. 10 is a longitudinal section of a water bag in its shrunk condition.

FIGS. 8 to 10 illustrate a third embodiment of the invention which utilizes an X-ray unit (already provided in the hospital) as the measuring apparatus. Specifically, the X-ray unit includes an X-ray emitter 32 on which a therapeutical energy generator 31 is detachably mounted. The emitter 32 is movable up and down above a surgical bed 33 and has an arm-shaped mounting member 48 secured thereto at a downward angle. The generator 31 is detachably mounted on the mounting member 48 by mounting screws 49. The generator 31 is of a high tension discharge type and includes an external housing 39 having a focussing reflector 40 disposed in its free end. The reflector has an elliptical surface. A discharge electrode 42 is located at one of the foci of the elliptical surface, and the opening of the reflector 40 is covered by a flexible water bag 41 which is filled with a shock wave transmitting medium 43 such as water, thus filling the space between the external surface of a patient 50 and the discharge electrode 42. Piping 44, 45 inside of the housing 39 supplies or discharges water to and from the bag 41. The electrode 42 is connected through a connection cord 46 passing through the housing 39 to a source of high tension 34, whereby a discharge voltage may be applied to the electrode. An ultrasonic probe 47 (which is used as an auxiliary measuring apparatus) is located along the underside of the housing 39.

The X-ray emitter 32 is supported by a support member 36 to be movable vertically above the surgical bed 33. The bed is conventionally horizontally translatable in two dimensions. The X-ray is transmitted through the patient 50 lying on the bed to be received by an X-ray receptor or an image intensifier 35 (including photomultipliers) located below the bed 33. The arrangement may include a monitor 37 which indicates the focus of the shock wave and an X-ray monitor 38. The patient's kidney 50 is indicated at 51, with a calculus 52 located therein.

In operation, when the energy generator 31 is mounted on the X-ray measuring apparatus, the system is adjusted so that the axes of ultrasonic energy and X-ray radiation intersect each other at the calculus 52, as indicated in FIG. 9. The apparatus is connected to the source 34 and to a source of water, not shown, through the piping 44, 45. The patient 50 then lies on the bed 33. The X-ray unit is then operated to cause the X-ray to pass through the kidney 51 to observe and detect the calculus 52. At this time, the water bag 41 should be shrunk as indicated in FIG. 10 to approach the opening of the reflector 40, by removing the water therefrom, to prevent the bag from interfering with the X-ray unit. After the calculus 52 is detected, the water is supplied to the water bag 41 to expand it, and the support member 36 is operated to bring the bag into close contact with the patient. While observing the monitor 37, the location of the calculus 52 is brought to the other focal point of the elliptical reflector 40. A high tension is then applied to the electrode 42 to cause its discharge, whereupon shock wave energy is focussed upon the calculus 52 located within the kidney 51, thus fracturing it as intended to allow it to be digested in a natural manner.

While the apparatus may be used in combination with an X-ray unit to detect the location of a calculus, the location of a calculus may also be detected by an ultrasonic probe 47 mounted on a housing 39. In addition, the energy generator 31 may be detachably mounted on the image intensifier 35 of the X-ray unit with a similar effect.

Figure 11:
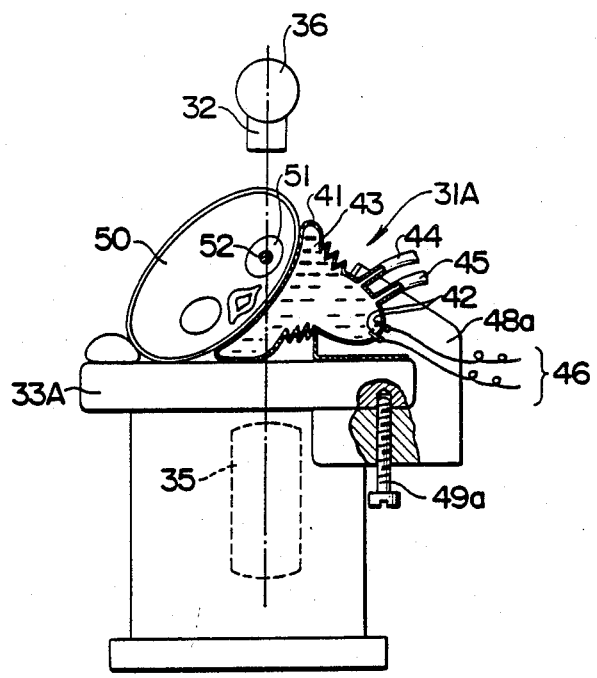
FIG. 11 is a schematic view, partly in longitudinal section, of an apparatus according to a fourth embodiment of the invention.

FIG. 11 is a longitudinal section through an apparatus according to a fourth embodiment of the invention, which is similar to the apparatus illustrated in FIGS. 8 and 9. Accordingly, similar parts are designated by corresponding numerals without repeating their description. Specifically, the only difference between the embodiments is that a therapeutical energy generator 31A is detachably mounted on the surgical bed in distinction to the energy generator 31 which is detachably mounted on the X-ray emitter 32 or the image intensifier 35 in the embodiment of FIGS. 8 and 9. Thus, referring to FIG. 11, the generator 31A is detachably mounted on a surgical bed 33A by mounting screws 49A with a mounting member 48A interposed therebetween. When the energy generator is directly mounted on the bed 33A, the generator 31A may be more firmly secured to improve stability during use. The apparatus functions in a similar manner and achieves a similar effect as the apparatus illustrated in FIGS. 8 and 9.

Figure 12:
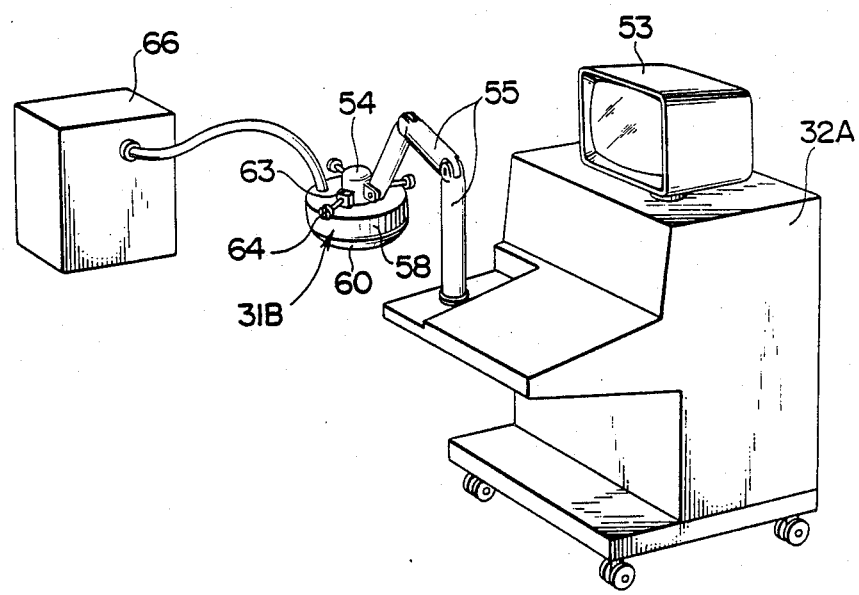
FIG. 12 is a perspective view of an apparatus according to a fifth embodiment of the invention.

FIG. 12 is a schematic illustration of an apparatus according to a fifth embodiment of the invention which is used in combination with an existing ultrasonic diagnostic apparatus utilized as a measuring apparatus, with a therapeutical energy generator detachably mounted thereon. Specifically, FIG. 12 illustrates a therapeutical energy generator 31B, an ultrasonic diagnostic observation apparatus 32A, an observation monitor 53, an ultrasonic probe of mechanical scan type associated with the apparatus 32A, and an arm 55 which carries the probe 54 in a movable manner. As illustrated, the ultrasonic diagnostic apparatus 32A is free to move above, and the probe 54 may be freely positioned relative to an affected part 57 of a patient 56 (see FIG. 13) by means of the arm 56.

Figure 13:
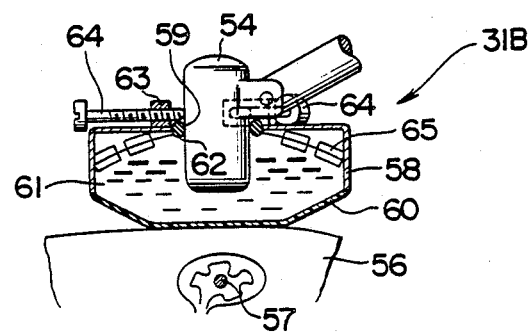
FIG. 13 is an enlarged, fragmentary cross sectional view of the apparatus illustrated in FIG. 12.

Referring to FIG. 13, the therapeutical energy generator 31B includes a body 58 in the form of a cup-shaped casing having an opening 59 centrally in its top in which the probe 54 is fitted and having a bottom opening which is closed by a water bag 60. An array of piezoelectric elements 65 is disposed along a spherical surface on the internal upper surface of the body 58. The water bag 60 is filled with water 61 acting as an ultrasonic wave transmitting medium, and an O-ring 62 is fitted around the top opening 59 to maintain the body 58 watertight against the probe 54. The top of the body 58 is integrally formed with three threaded lugs 63, which are engaged by mounting screws 64 to permit the apparatus 31B to be detachably mounted on the probe 54 of the ultrasonic diagnostic apparatus 32A. The piezoelectric elements 65 are connected to a drive unit 66, and shock wave energy generated by the piezoelectric elements 65 is focussed upon the affected part 57 (such as the calculus of the patient 56) for fracturing it.

In use, the therapeutical energy generator 31B is mounted on the probe 54 of the ultrasonic diagnostic apparatus 32A by the mounting screws 64, and the piezoelectric elements are connected to the drive unit 66. The generator 31B is located relative to the affected part 57 of the patient 56 with the surface of the water bag 60 in close contact therewith as illustrated in FIG. 13. The probe 54 detects the affected part, such as a calculus, and then the affected part 57 is brought to the focal point of the array of piezoelectric elements 65. A drive voltage is then applied to the piezoelectric elements 65 from the drive unit 66 to generate a shock wave, which is focussed upon the affected part 57 to fracture it. In this manner, the apparatus of the present embodiment operates similarly and achieves a similar effect as the apparatus of the third and the fourth embodiments.

Figure 14:
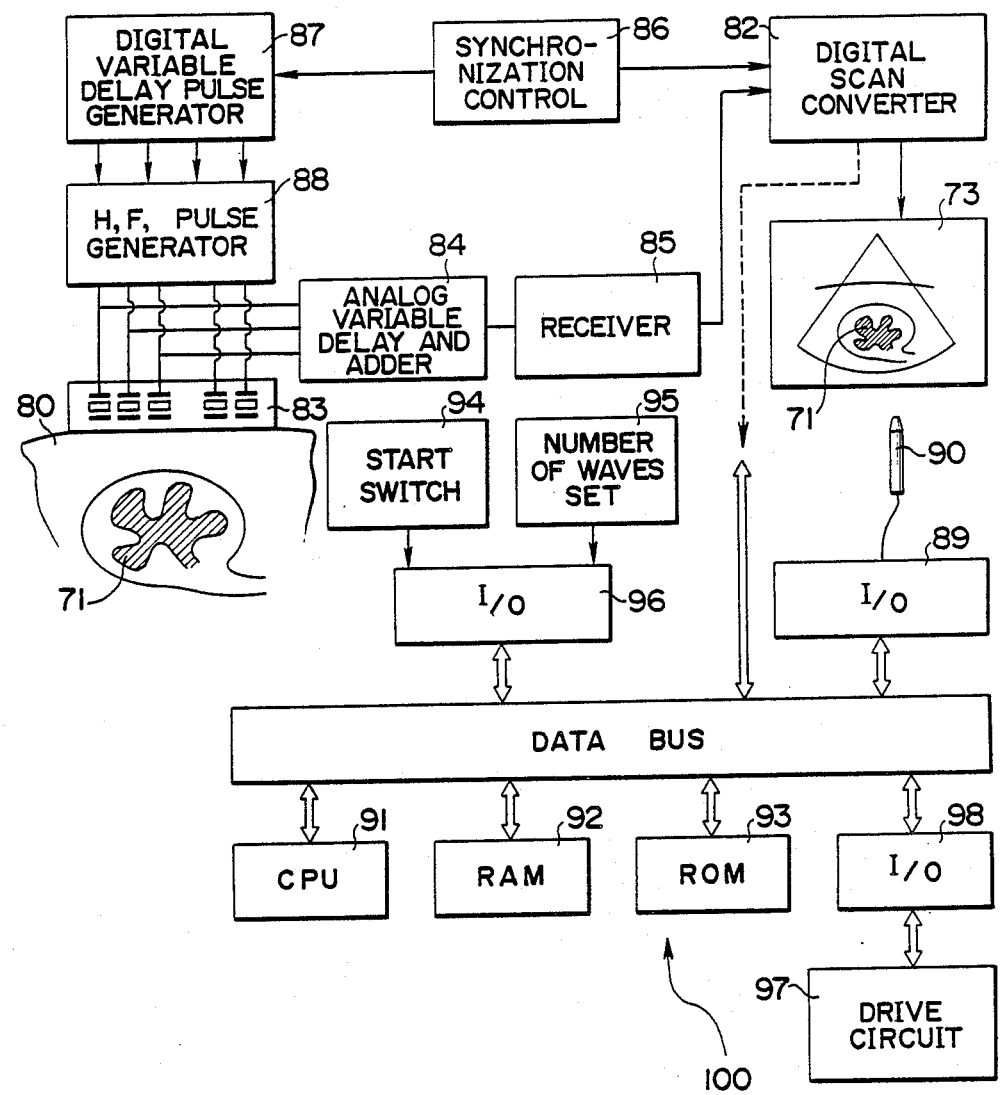
FIG. 14 is a block diagram of an apparatus according to a sixth embodiment of the invention.

FIG. 14 illustrates an apparatus according to a sixth embodiment of the invention which is designed for use when a calculus is susceptible to motion (as by breathing) at the instant when the calculus is targeted.

Specifically, a monitor display 73 is fed with a calculus location signal from a digital scan converter 82 for displaying an image of the calculus. A calculus 71 within a patient 80 is detected by an ultrasonic detector 83, which feeds a signal to the converter 82 through a analog variable delay and adder 84 and a receiver 85. A digital variable delay pulse generator 87 is then synchronized with the converter 82 through a synchronization control circuit 86, and controls a high frequency pulse generator 88, which feeds the ultrasonic detector 83. The detector 83 includes a planar array of elements, and hence the delay pulse generator 87 is used to delay pulses for the purpose of focussing.

A positioning signal (such as from a light pen 90) is fed through I/O port 89 to be stored in a control memory 100 (which includes CPU 91, RAM 92 and ROM 93) so as to be delivered to the display 73 at suitable times. A shock wave start switch 94 and a number of shock waves presetting circuit 95 are connected to the memory through I/O port 96, and a shock wave generator drive circuit 97 is connected to a data bus through an I/O port 98.

Figure 15:
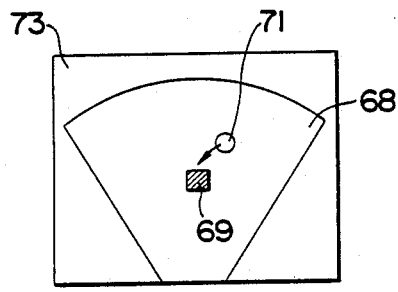
FIG. 15 is an illustration of a monitor screen of a display unit illustrated in FIG. 14.
Figure 16:
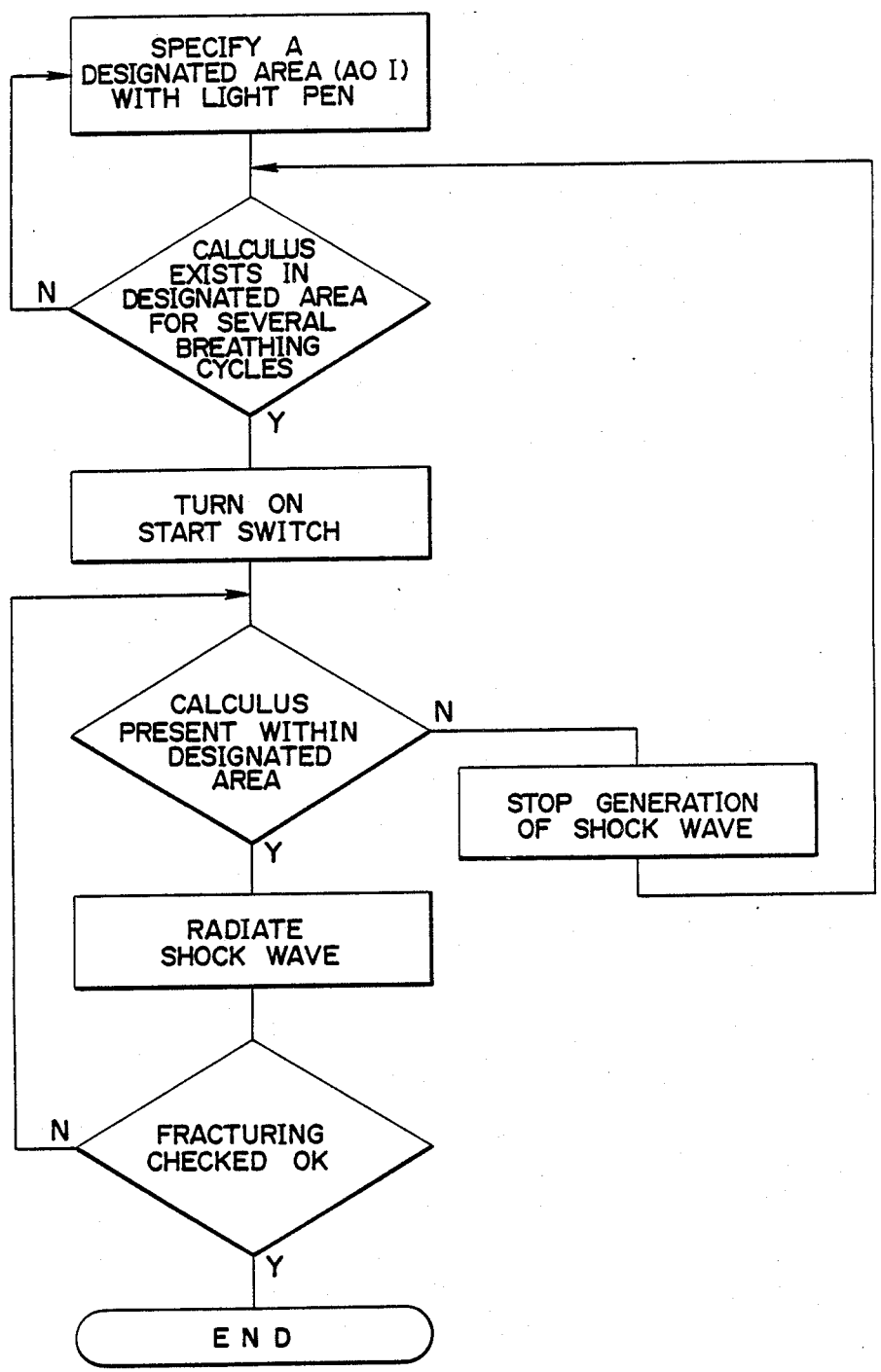
FIG. 16 is a flowchart illustrating the operation of an apparatus according to the invention.

Operation of the apparatus illustrated in FIG. 14 will be described below with reference to FIGS. 15 and 16. The location of the calculus 71 is detected by a measuring apparatus, not shown and its image is displayed to allow a recognition of the number of calculi, its or their size, configuration and location. Such information is displayed on the monitor screen of the display 73 in a designated area. A region 68 subject to determination by an ultrasonic observation apparatus is indicated on the monitor screen of the display 73, as indicated in FIG. 15. Observing calculus information displayed on the monitor screen, an operator (such as a physician) specifies a designated area 69 (an area of interest-AOI) by the light pen 90. This information is fed to and stored in the control memory 100 through the I/O port 89.

When the shock wave start switch 94 of FIG. 14 is turned on to fracture the calculus, the ultrasonic fracturing operation is initiated at the point in time when the designated area 69 stored in the control memory 100 coincides with the specified location of the calculus 71 (which is determined by the ultrasonic measuring apparatus). Thus, CPU 91 triggers the shock wave generator drive circuit 97 a predetermined number of times (preset in the circuit 98), through the data bus and I/O port 98. Each time the drive circuit 97 is triggered, the ultrasonic shock wave is emitted and directed to the calculus 71 at the specified location within the coeloma. If the calculus 71 goes outside the specified area during the fracturing operation or when the calculus 71 is out of the specified area from the beginning, CPU 91 does not deliver a trigger pulse if the start switch 94 is turned on. The calculus 71 to be treated can be recognized by a portion of ultrasonic data from the digital scan converter 82 which is above a threshold value and which is located within an area specified by the operator on the monitor screen of the display 33 by the light pen 90. Accordingly, if the calculus moves out of the specified area due to a breathing operation, the ultrasonic shock wave generator is turned off, thus avoiding a wasteful shock wave emission.

Figure 17:
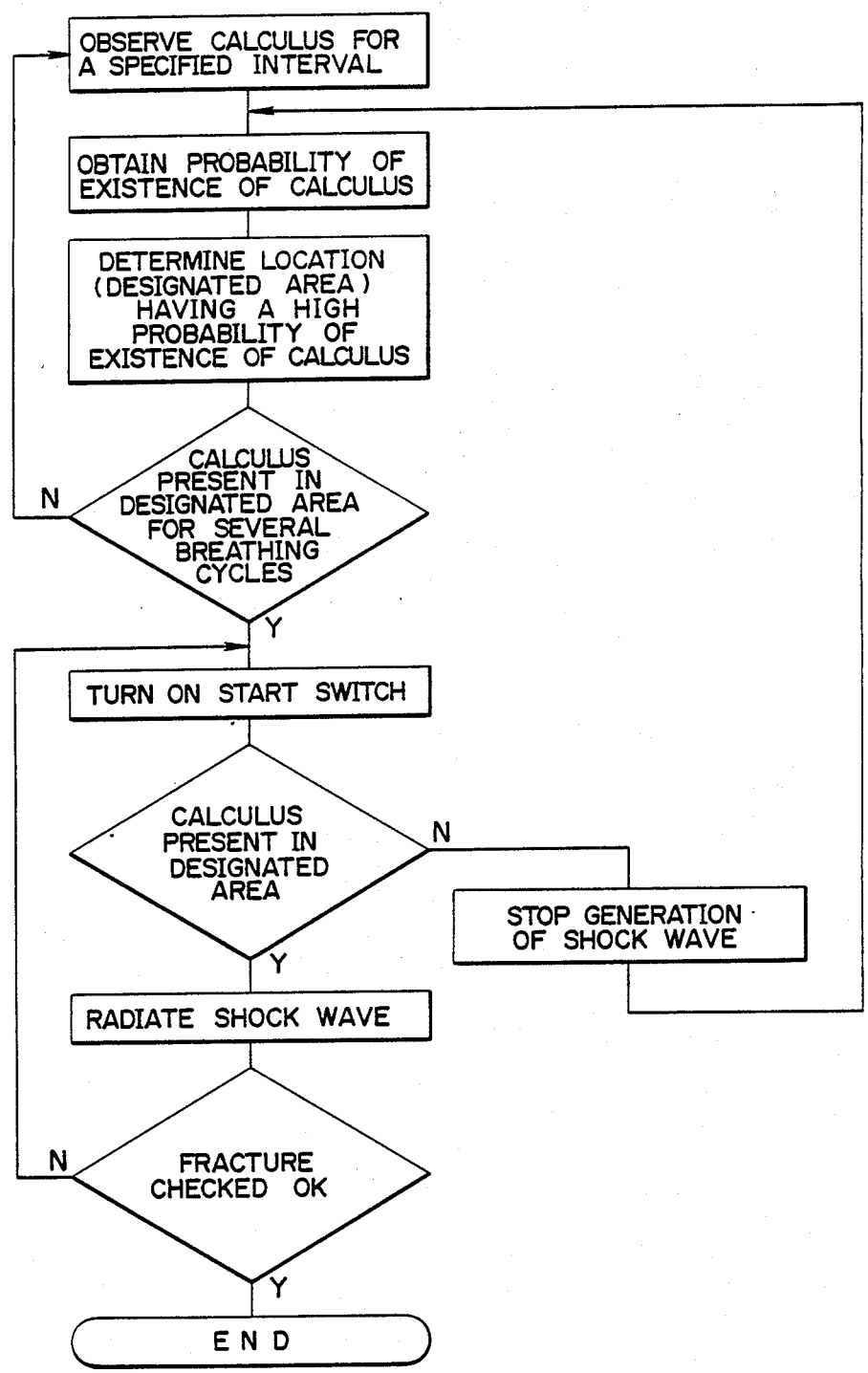
FIG. 17 is a flowchart illustrating the operation of an apparatus according to a seventh embodiment of the invention.

FIG. 17 is a flowchart for a seventh embodiment of the invention. Considering a renal calculus by way of example, movement of the calculus 71 due to breathing has a regular periodicity. Accordingly, when the calculus 71 is observed by the ultrasonic measuring apparatus for a given time interval, the probable location of the calculus 71 can be determined. Thus, by adding data stored in a frame memory (RAM 92) together over a given time interval, data representing a location where the calculus 71 exists for a longer time provides a greater sum, and is more intensely displayed on the display 73. In this manner, a distribution of the probability of the location where the calculus 71 exists is obtained. The location where the probability of the existence of the calculus 71 is high is then recognized, and the specified area 69 is specified on the monitor screen of the display 73 by the light pen 90.

The ultrasonic shock wave is irradiated upon coincidence between the location of the calculus 71 (determined by the ultrasonic measuring apparatus) and the specified area 69, but the shock wave generator cannot be turned on in the absence of such coincidence. In this manner, the shock wave generator is turned on only when the calculus is where the probability of existence of the calculus 71 is at its maximum.

The target to be treated is not limited to the calculus 71 alone, nor is the invention limited to a calculus fracturing apparatus. The invention is equally applicable to any therapeutical apparatus in which it is desired to focus an ultrasonic wave upon a target.

Figure 18:
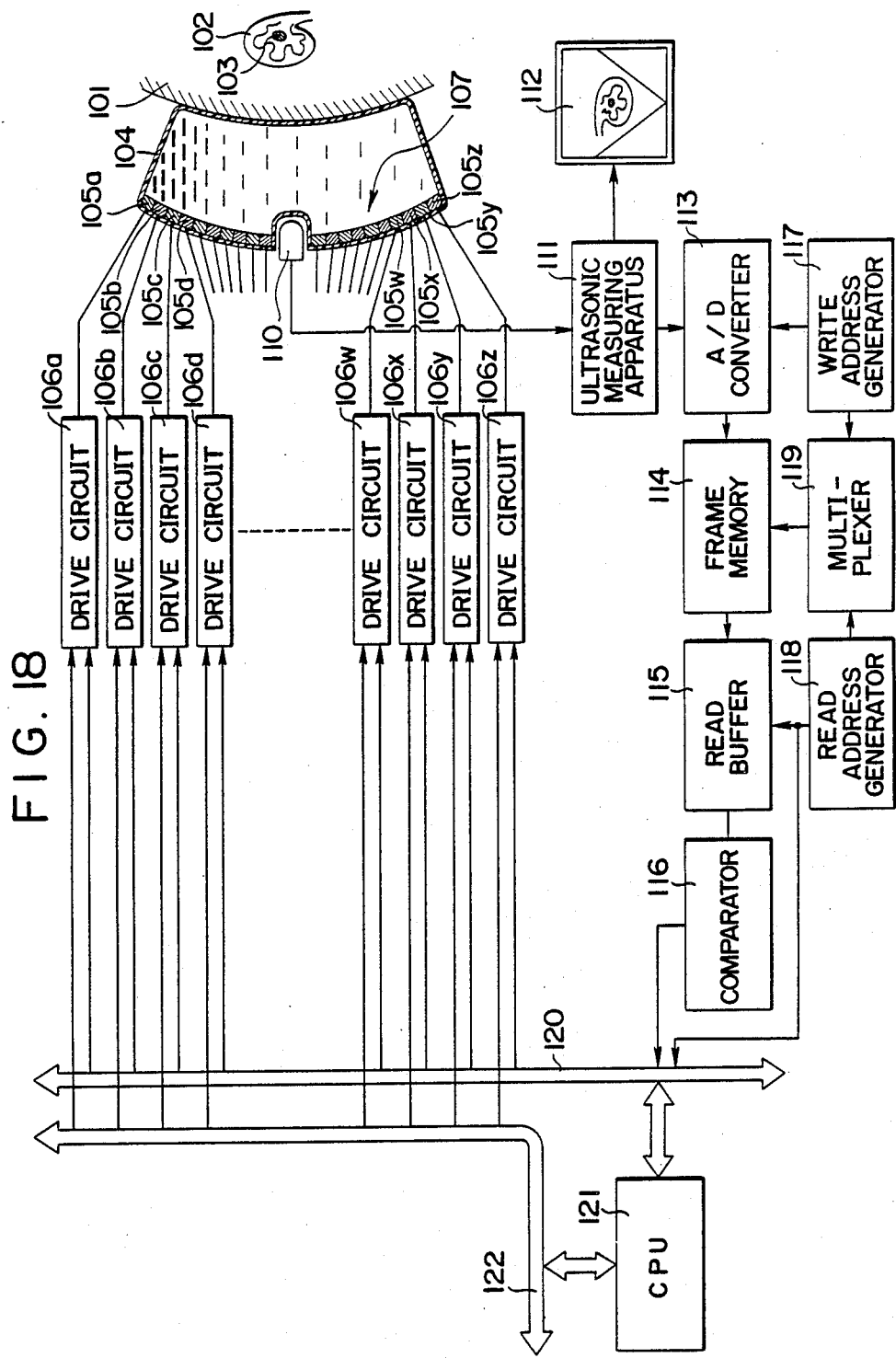
FIG. 18 is a block diagram of an apparatus according to an eighth embodiment of the invention.

FIG. 18 illustrates an apparatus according to an eighth embodiment of the invention which enables the focal point of the ultrasonic shock wave to be shifted simply and rapidly. A body 101 includes a kidney 102 in which a calculus 103, the target to be treated, is located. To fracture the calculus 103, a shock wave generator 107 (including an array of ultrasonic vibrators 105a to 105z disposed along a spherical surface in a mosaic pattern) contacts the body 101 with a water-filled bag 104 interposed therebetween. A number of vibrators 105a to 105z (greater than the number illustrated in FIG. 18) may be employed.

Each of the ultrasonic vibrators 105a to 105z is connected to one of the drive circuits 106a to 106z, each of which applies a drive voltage to its associated vibrator to cause the latter to generate an ultrasonic shock wave. An ultrasonic probe 110 (of mechanical scan type) is located at the center of the vibrators 105a to 105z. The probe 110 is connected to an ultrasonic measuring apparatus 111, which feeds its output to CRT monitor 112, and an A/D converter 113. An output from the converter 113 is written into a frame memory 114. The frame memory 114 includes a memory area which corresponds to the screen of the monitor 112. Data read out of the memory 114 is fed through readout buffer circuit 115 to a comparator 116. A multiplexer 119 (which switches between outputs of a write address generator 117 and a read address generator 118) is connected to the memory 114. An output from the comparator 116 and an output from the read address generator 118 are fed through a data bus 120 to CPU 121.

An address bus 122 is connected to CPU 121, and both the address bus 122 and the data bus 120 are connected to the drive circuits 106a to 106z. Peripheral circuits associated with CPU 121 such as memories, clock circuits and a power supply for the drive circuits 106a to 106z are omitted from the illustration.

In operation, the ultrasonic probe 110 performs a sector scan with its ultrasonic wave output to derive an echo signal from the living body 101, kidney 102m and calculus 103 with the shock wave generator 107 in contact with the body 101 and with the bag 104 interposed therebetween The echo signal is processed in the ultrasonic measuring apparatus 111 to derive a signal which represents a tomographic image of an object being examined, and the tomographic image signal is displayed on CRT monitor 112. The tomographic image signal output from the apparatus 111 is fed to the converter 113, and each picture element signal is written into the frame memory 114. At this time, the multiplexer 119 selects an output from the write address generator 117, thus supplying a series of write addresses to the memory 114.

When data representing one frame of tomographic image has been written into the memory 114, the multiplexer 119 switches to select an output from the read address generator 118, thus reading data from the memory and supplying it to the comparator 116 through the buffer 115. The comparator 116 determines that a particular picture element in the frame represents the surface of the body 101 when its corresponding signal exceeds a threshold value. In response to addresses of those picture elements which represent the surface of the body 101 and supplied to CPU 121 through the data bus 120, CPU 121 operates to determine the distance from the surface of the body 101 to the location of the calculus 103 within the kidney 102. It then calculates the distance from the shock wave generator 107 to the focal point of the ultrasonic shock wave. CPU 121 then activates selected ultrasonic vibrators for emission of an ultrasonic shock wave, depending on the distance calculated. For example, for a near distance, the vibrators 105a to 105q are selected, and for a medium distance, the vibrators 105f to 105u are selected. The selection of particular ultrasonic vibrators is equivalent to choosing an aperture radius of the shock wave generator 107. Changing the aperture radius of the shock wave generator 107 changes the focal point of the ultrasonic shock wave, thus allowing the focal point of the ultrasonic shock wave to be coincident with the calculus 103. This aspect will be dealt with in more detail.

The acoustical field of a circular concave-surface vibrator is very complex. However, Rayleigh's formula describes sound pressure on a central axis relative to mean sound pressure on a radiating surface as follows:

$$P_A = \left| \frac{P_A}{P_O} \right| = \left| \frac{2R}{R-Z} \sin \left[ \frac{\pi}{2} \cdot \frac{a^2}{\lambda R^2} \cdot \frac{R-Z}{2} \right] \right|$$

Where R represents the radius of curvature, $\lambda$ the wavelength in a medium, a the radius of a vibrator and Z the distance to the focal point. While the formula appears to be complicated in nature, it may be assumed that R, $\lambda$ and $P_A$ are constants, thus reducing the formula to a relationship between a and z. Thus, assuming that the radius of curvature, the drive frequency and the sound pressure are constant, the distance z to the focal point of the ultrasonic shock wave may be changed by changing the radius of the vibrator. By way of example, when a drive frequency of 300 kHz and a radius of curvature of 100 mm are used, changing the radius of the vibrator in a range from 13 to 28 mm results in changing the distance to the focal point from about 20 mm to 115 mm. Thus, a number of ultrasonic vibrators to be driven may be chosen depending on the distance. If the calculus 103 is located nearer the shock wave generator 107, a smaller aperture radius may be chosen for the shock wave generator 107. Conversely, when the calculus 103 is located further from the generator 107, a larger aperture radius may be chosen. In this manner, the focal point of the ultrasonic shock wave may be brought into coincidence with the location of calculus 103. When a reduced aperture radius is used, the number of driven vibrators decreases, thus decreasing the power available at the focal point of the shock wave. However, the voltage applied to each driven vibrator may be increased, thus feeding greater power to each vibrator to achieve equal power at the focal point, thus maintaining fracturing power at the same level. In this manner, the eighth embodiment permits the focal point of a shock wave to be freely changed in the radial direction or in the direction of depth by merely increasing or decreasing the number of vibrators without an accompanying movement of the shock wave generator 107.

If the calculus 103 moves in response to breathing, the ultrasonic measuring apparatus 111 is able to index such location as mentioned previously, and hence CPU 121 can choose a particular group of ultrasonic vibrators which are to be driven, thus maintaining the focal point of the shock wave coincident with the location of the calculus. This embodiment is also applicable to any arrangement in which an ultrasonic wave must be focussed upon a target to be treated.

Figure 19:
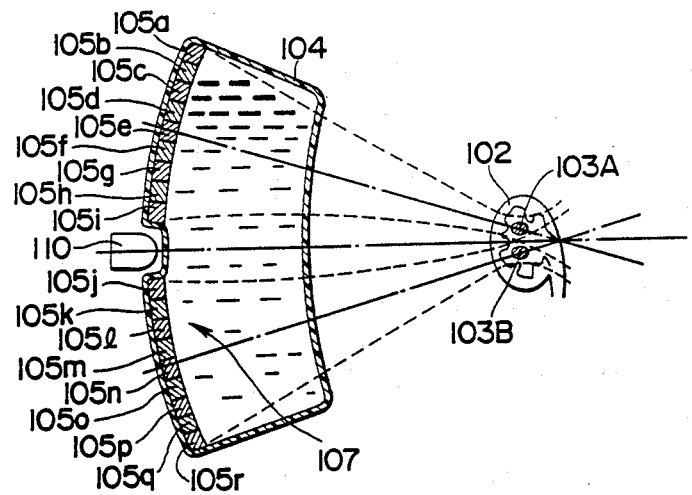
FIG. 19 is a fragmentary cross sectional view of an apparatus according to a ninth embodiment of the invention.

FIG. 19 shows an essential part of a ninth embodiment of the invention. When a particular group of ultrasonic vibrators, 105a to 105i, for example, are centered about an ultrasonic vibrator 105e, the focal point of the ultrasonic shock wave may be located at an upper focal point 103A (FIG. 19). Alternatively, when a group of ultrasonic vibrators 105j to 105r centered about an ultrasonic vibrator 105n is chosen, the focal point of the shock waves shifts to a lower focal point 103B (FIG. 19). In this manner, an equal number of ultrasonic vibrators located on either side of a particular ultrasonic vibrator may be freely driven to shift the focal point of the ultrasonic shock wave generator 107 in the same direction as the shock wave generator 107. The general arrangement (including ultrasonic measuring apparatus and data bus) remains the same as in the eighth embodiment, and hence is omitted from illustration.

Figure 20:
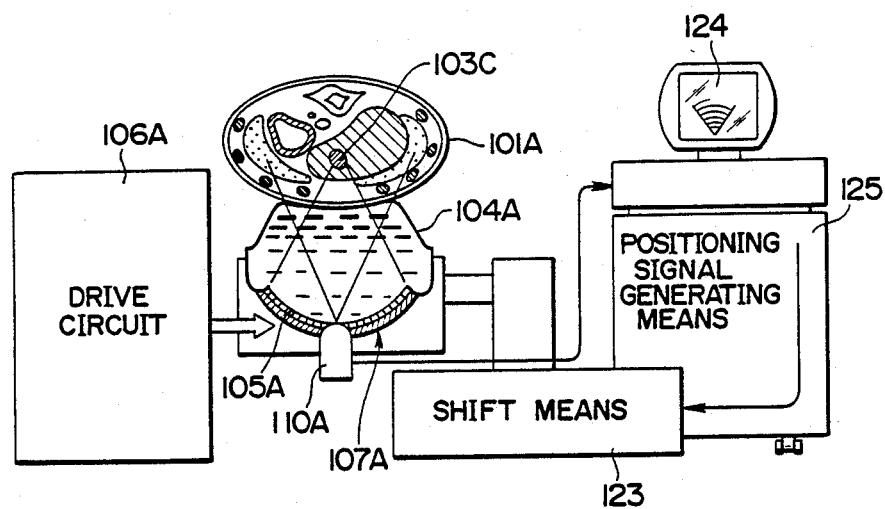
FIG. 20 is a schematic illustration of an apparatus according to a tenth embodiment of the invention.

FIG. 20 illustrates a tenth embodiment of the invention. Specifically, a shock wave generator 107A including a water bag 104A filled with water is connected to a drive circuit 106A and carried by shift means 123. The location of a calculus 103C within a living body 101A is recognized by the combination of an ultrasonic probe 110A and ultrasonic measuring apparatus 124, and the shock wave generator 107A is moved through an increased stroke by means of positioning signal generator 125 and the shift means 123 in order to bring the focus of the generator 107A into coincidence with the calculus 103C. The focus of the generator 107A is only temporarily brought into coincidence with the calculus 103C and the calculus 103C continues to change its position due to breathing. This makes it difficult to maintain the focus of the generator 107A upon the calculus 103C. Accordingly, ultrasonic vibrators 105A contained in the generator 107A are selectively driven in the same manner as described above in connection with the eighth and the ninth embodiment to shift the focal point of the ultrasonic shock wave, thereby bringing the focal point into alignment with the calculus 103C. In this manner, the focal point of the ultrasonic shock wave moves through an increased stroke by the shift means 123 which carries the generator 107A, and is rapidly moved through a reduced stroke by a selective energization of particular driven ultrasonic vibrators.

Figure 21:
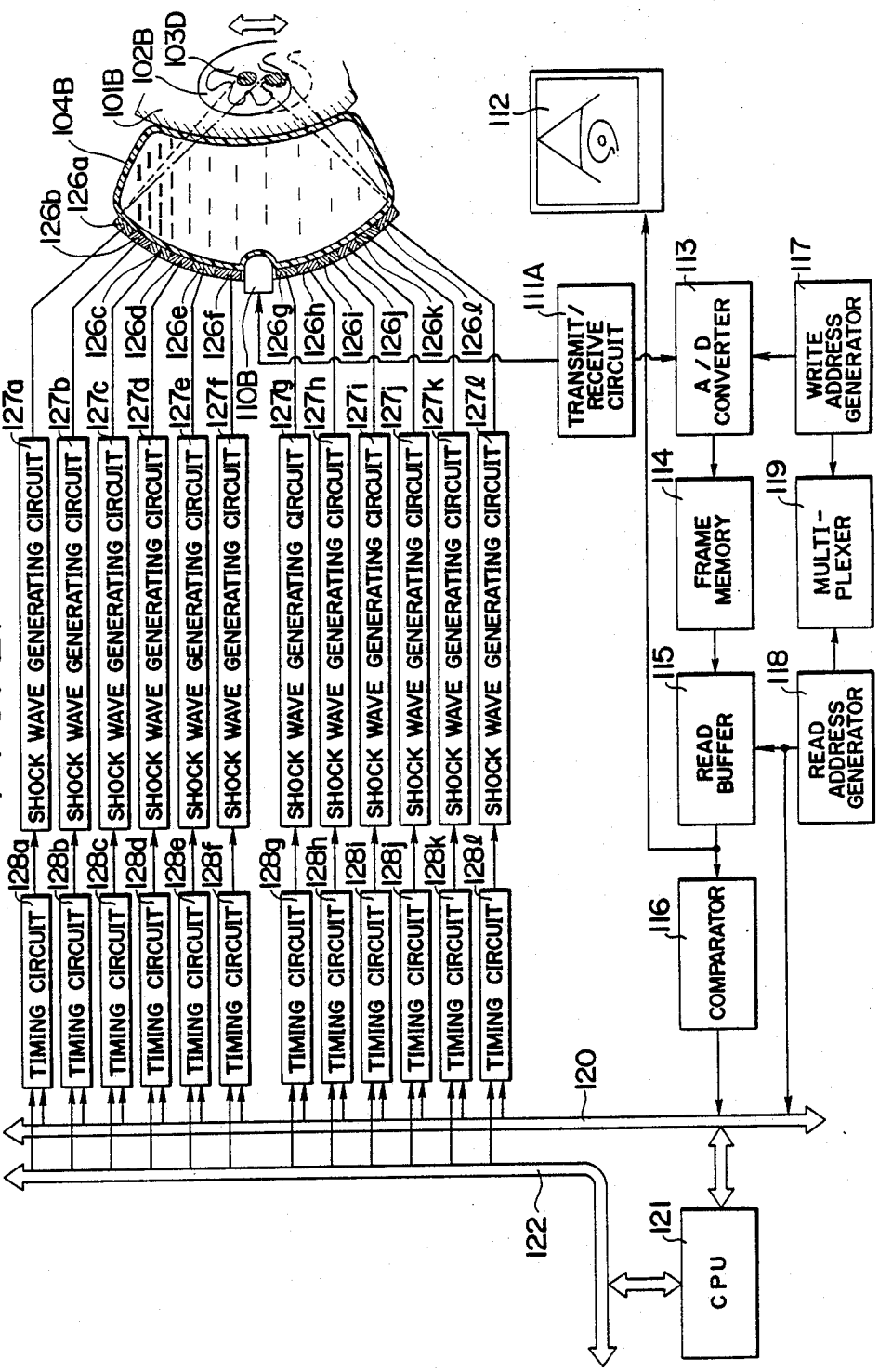
FIG. 21 is a block diagram of an apparatus according to an eleventh embodiment of the invention.

FIG. 21 illustrates an apparatus according to an eleventh embodiment of the invention which is designed to concentrate the ultrasonic wave upon an affected area by controlling the timing of focussing of the ultrasonic waves developed by the ultrasonic vibrators. Specifically, a living body 101B includes a kidney 102B in which a calculus 103D to be treated is situated. In order to fracture the calculus 103D, a probe with piezoelectric elements 126a to 126l disposed along a quadratic surface in a mosaic pattern is brought into contact with the living body 101B with a water bag 104B filled with water interposed therebetween. A number of piezoelectric elements greater than those illustrated are actually used. The illustration is simplified for convenience. Piezoelectric elements 126a to 126l are connected to shock wave generating circuits 127a to 127l, respectively, which apply a pulse voltage to the associated elements 126a to 126l to cause the latter to produce a shock wave of an increased intensity sufficient to destroy the calculus. The generating circuits 127a to 127l are connected to timing circuits 128a and 128l, respectively, which control the timing of the shock wave.

The piezoelectric elements 126a to 126l are disposed along an arc, and an ultrasonic probe 110B of mechanical scan type is disposed between the central piezoelectric elements, namely, 126f, 126g, for the purpose of observation. The probe 110B is connected to a transmit/receive circuit 111A. When a transmission signal is delivered from the circuit 111A to the probe 110B, the latter produces an ultrasonic beam which is directed toward a coeloma, and the beam which is reflected by the calculus 103D located within an affected part is received by the probe 110B and then fed to the receive circuit 111A, thus allowing the location of the calculus 103D to be detected. The reception output from the circuit 111A is supplied to an A/D converter 113.

Selected signals processed by the circuit 111A are fed to CPU 121, and the memory cycle takes place in substantially the same manner as described above in connection with the eighth embodiment shown in FIG. 18, and therefore will not be specifically described, except to note that corresponding parts are designated by like reference numerals. An address bus 122 and a data bus 120 are connected to the timing circuits 128a to 128l.

In operation, the probe (with the piezoelectric elements 126a to 126l) is brought into contact with the body 101B through the interposed water bag 104B. The probe 110B performs a sector scan, thus deriving an echo signal from the body 101B, the kidney 102B and the calculus 103D. The echo signal is processed by the transmit/receive circuit 111A, and fed through a frame memory 114 to derive a signal representing a tomographic image of an object being examined. The tomographic image is displayed on CRT display 112. While observing the display 112, an operator adjusts the location of the water bag and the probe, so that the focal point of the quadratic surface along which the piezoelectric elements 126a to 126l are disposed coincides with the calculus 103D. Such adjustment takes place by a system disclosed in U.S. Pat. No. 4,617,931.

Data read from the frame memory 114 is fed through a read buffer circuit 115 to a comparator 116, which is operative to extract the addresses of only those signals having levels greater than a given value, and these addresses are fed to the data bus 120 together with data from the read address generator 118. In this manner, CPU 121 stores the addresses of only those signals having a high brightness. The extracted addresses represent a digital value indicative of the location of the calculus. The timing with which the piezoelectric elements 126a to 126l are driven are adjusted to focus the ultrasonic beam produced by these elements upon the focus thus determined.

Figure 22:
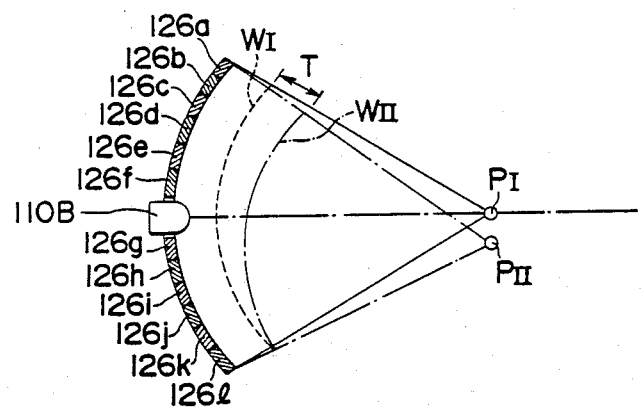
FIG. 22 is a diagram illustrating the relationship between the wave surface and the focal point in the arrangement illustrated in FIG. 21.

FIG. 22 graphically illustrates the steps of bringing and maintaining the focal point of an ultrasonic beam emitted by the piezoelectric elements 126a to 126l into and in coincidence with the location $P_I$ or $P_{II}$ of the calculus 103D. An ultrasonic wave transmitting surface with a two-dimensional spherical shell is developed in front of the piezoelectric elements 126a to 126l as indicated in dotted lines in FIG. 22. Assuming that the focal point of the ultrasonic wave having the wave surface $W_I$ coincides with the location of $P_I$ of the calculus, if the calculus 103D moves from the location $P_I$ to $P_{II}$ (as a result of breathing, for example) the focal point must be rapidly moved from $P_I$ to $P_{II}$, thus displacing the transmitting wave surface $W_I$ to another transmitting surface $W_{II}$. In order to achieve the wave surface $W_{II}$, the timing of a signal applied to the piezoelectric element 126a is chosen to be earlier than the timing of a signal applied to the piezoelectric element 126l by a time interval T. The same is true with respect to the remaining 126b to 126k.

Figure 23:
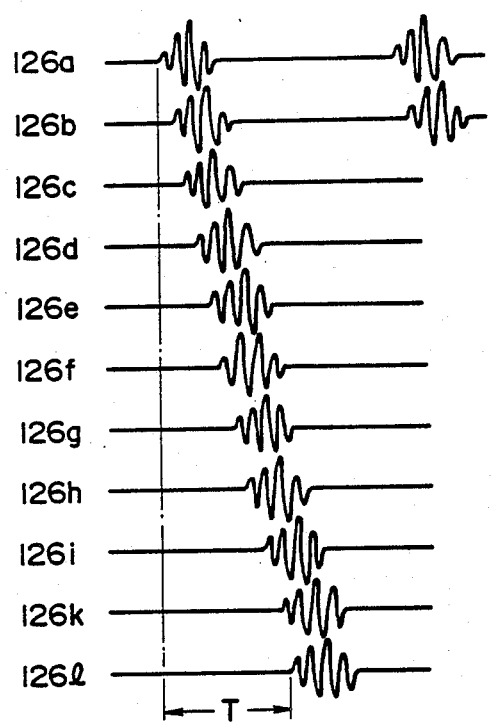
FIG. 23 graphically illustrates the waveforms of ultrasonic signals from individual piezoelectric elements used in the arrangement of FIG. 21.

Signals which drive the piezoelectric elements 126a to 126l are derived by the shock wave generating circuits 127a to 127l, in a manner illustrated in FIG. 23. The relative timing between the signals applied to the individual piezoelectric elements is determined by the timing circuits 128a to 128l by signals delivered from CPU 121 over the data bus 120. In this manner, a time difference T between the wave surfaces $W_I$ and $W_{II}$ is achieved.

Figure 24:
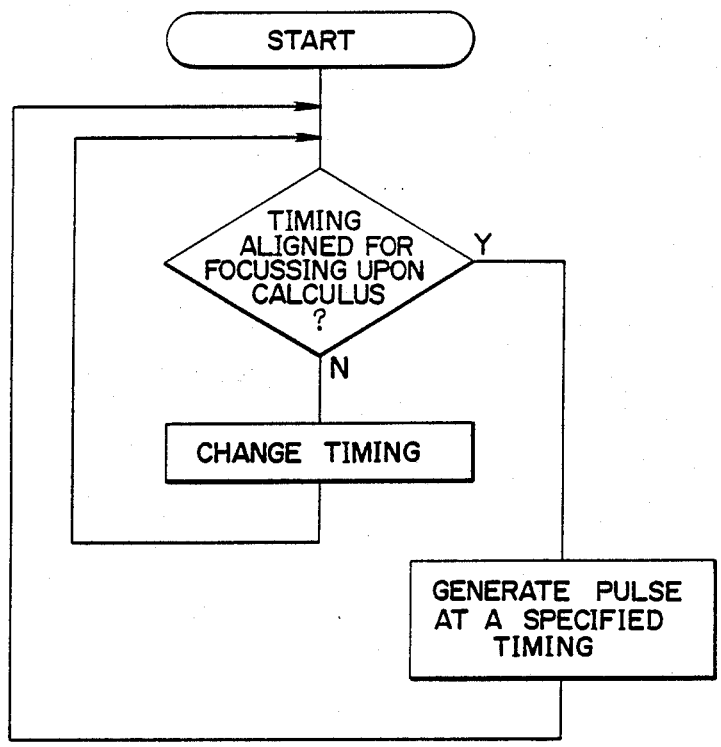
FIG. 24 is a flowchart of the operation of the arrangement illustrated in FIG. 21.

FIG. 24 is a flowchart of a timing control. Specifically, the location of a calculus is compared against a focal point predicted from the prevailing timing. If a coincidence therebetween is not reached, the timing is modified, while the present timing is used to develop pulses if the coincidence is maintained. In this manner, the timing of the driving of the individual piezoelectric elements which are distributed in three dimensions along a spherical surface in a mosaic pattern is controlled to achieve a focal point which automatically tracks the calculus.

In this manner, in accordance with this embodiment, data representing a location of an affected area is derived by means which continuously operate to detect the location of such area. Such data is utilized to drive focussing means to bring the focal point into coincidence with the affected area, the focusing means controls the timing with which the individual piezoelectric elements are driven. In this manner, focussing is accomplished without any time lag in the presence of a movement of the affected area, thus improving the efficiency with which a calculus is fractured. Furthermore, normal tissues are not damaged.

Figure 25:
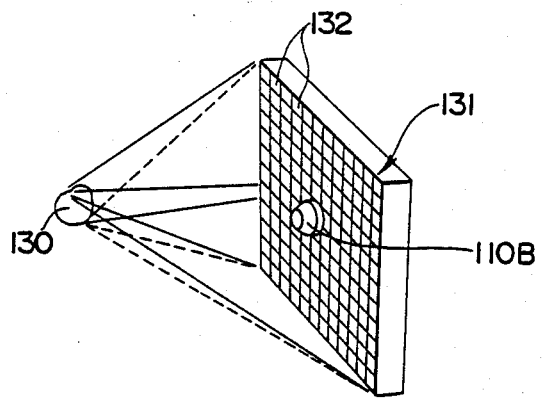
FIG. 25 is a perspective view of an apparatus according to a twelfth embodiment of the invention.

FIG. 25 is an illustration of part of a twelfth embodiment of the invention which is designed for thermal therapy of a tumor. In this embodiment, the arrangement is generally similar to the eleventh embodiment except that a number of piezoelectric elements 132 are disposed in a matrix forming a plane, thus constituting together a group 131 thereof. An ultrasonic probe 110B is disposed at the center of the matrix to detect the location of a tumor 130, and the group of piezoelectric elements 131 emits an ultrasonic beam which is directed toward the tumor 130 for thermal therapy thereof. Where the tumor 130 has an extensive area, a scan of the ultrasonic beam may be utilized.

Figure 26A:
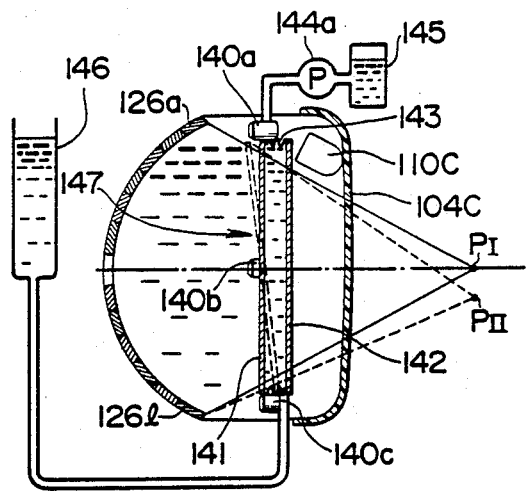
FIGS. 26A, B and C illustrate an apparatus according to a thirteenth embodiment of the invention.
Figure 26B:
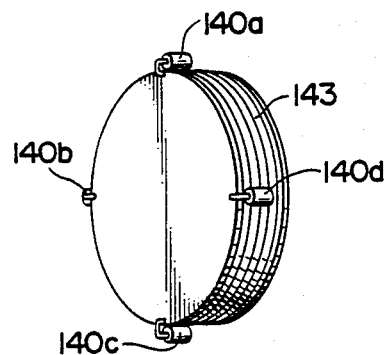
FIG. 26B being a perspective view of an acoustical prism.
Figure 26C:
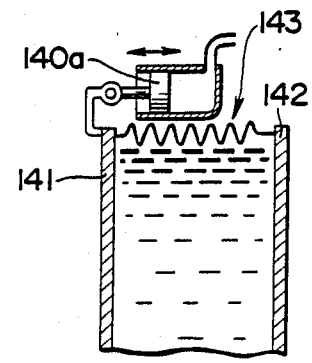
FIG. 26C being an enlarged, fragmentary cross sectional view of an acoustical prism.

FIGS. 26A to 26C illustrate a thirteenth embodiment of the invention which utilizes an acoustical prism to rapidly change the focal point of the ultrasonic shock wave. Referring to FIG. 26A, an acoustical prism 147 (with a pair of oppositely located lid plates 141, 142 of equal size and configuration and connected together by bellows 143) is contained within a water bag 104C. The internal space defined between the lid plates is filled with liquid having an acoustical refraction index greater than that of a liquid contained within the water bag 104C and supplied from a liquid tank 146. As illustrated in FIGS. 26A to 26C, four pistons 140a to 140d are located at an equal interval around the acoustical prism 147 to permit the spacing between the lid plates to be changed at will. Specifically, each of the pistons 140a to 140d includes a cylinder chamber which is connected through an associated pump 144a to 144d (144b to 144d not being shown) to an oil tank 125, as illustrated in FIG. 26A. The pumps 144a to 144d are controlled by a processor, not shown. An ultrasonic probe 110C for detecting the location of a calculus is disposed intermediate the acoustic prism 147 and the calculus.

In operation, movement of the calculus from location $P_I$ to a location $P_{II}$ is detected by the ultrasonic probe 110C, and an address signal corresponding to the location $P_{II}$ is fed to the processor mentioned above, which then responds thereto by calculating the orientation in which the ultrasonic beam is to be focussed, delivering the control signals fed to the pumps 144a to 144d. By activating the pistons 140a to 140d in a corresponding manner, the configuration of the acoustic prism 147 may be modified so that the ultrasonic beam is focused upon the location $P_{II}$ of the calculus. Thus, referring to FIG. 26A, when the lid plate 141 of the acoustical prism 147 is located as indicated by the solid line, the ultrasonic wave emitted by the piezoelectric elements 126a to 126l is focused upon the location $P_I$, but as the piston 140a projects while the piston 140c retracts into its cylinder to displace the lid plate 141 of the acoustical prism 147 to the dotted line position to thereby change the acoustic impedance, the focussing direction shifts downward, whereby the ultrasonic wave is focused on the location $P_{II}$. In this manner, the focal point of the ultrasonic wave may be changed rapidly, enabling a quick, automatic tracking operation. A change in the volume of the acoustical prism 147 takes place by increasing or decreasing the liquid quantity in the liquid tank 146.

FIG. 27 is a schematic illustration of an apparatus according to a fourteenth embodiment of the invention, which is designed to cover an extended area to facilitate determining the location of a calculus before it is treated. There is shown the physical body 151 of a patent which contains a calculus 152 therein. A pair of electronic scan type ultrasonic probes 153, 154 are used to obtain a tomographic image over an area encompassed by a pair of dotted lines 165, 166. The probe 153 is disposed for angular movement as by a probe driver 158 which may include a stepping motor, for example. On the other hand, the probe 154 is disposed for angular movement as well as for movement in three dimensions by a probe driver 158 (which may include a stepping motor or X-Y-Z stage). The probe 153 is located at the center of an ultrasonic wave generator 155 while the probe 154 is located at a lateral position adjacent thereto. The generator 155 includes a number of ultrasonic vibrators in an array along a spherical shell to produce an ultrasonic wave of an increased intensity at the focus F of the shell in response to a drive from a drive circuit 156. A water bag (not shown) formed of a soft resin material and filled with an ultrasonic wave transmitting medium such as water is interposed between the generator 155 and the patient 151.

An ultrasonic measuring apparatus 159 delivers a transmit pulse to the probes 153 and 154 through a rotary transformer 157, and a received pulse from the probes 153, 154 is fed through the transformer 157 back to the observation apparatus 159 so as to be displayed as a B-mode image. The rotary transformer 157 is conventional and permits an electrical signal to be transmitted to a rotating member without electrical contact. Image information from the measuring apparatus 159 is fed to an image processor 160 where the coordinates of the center of gravity of the calculus are calculated. A location detector 161 responds to a difference between the coordinates of the center of gravity and the coordinates of the focus F of the generator 155, by causing a position controller 162 to drive a shifting unit 163 to bring both points into coincidence.

In operation, when a tomographic image acquired by the probe 153 fails to locate a calculus, the probe 154 is initially rotated about its center axis 168 while causing it to revolve about the center axis 169 of the generator 155, thus causing it to scan across an extensive area in X, Y and Z directions to search for the calculus 152 within the patient 151. If the presence of a calculus is recognized in a certain tomographic image, such position information is utilized to cause the position controller 162 to drive the shifting unit 163 to move the location of the calculus 152 into a measurable range 165 having the focus F of the generator 155 on its center axis 169. After such movement, the location of the calculus 152 is automatically tracked on the basis of a tomographic image from the probe 153, covering the measurable range 165 for performing a fracturing operation.

Specifically, an ultrasonic echo signal from the probe 153 is fed through the rotary transformer 157 to the measuring apparatus 159 where a B-mode image is obtained. This information is then fed to the image processor 160 where digitization and calculation of an area are made to extract the position of the center of gravity of the calculus 152 which is then delivered to the location detector 161. The location detector 161 detects a difference between the location of the center of gravity and the location of the focus F, and the difference signal is output to the position controller 162. The position controller 162 drives the shifting unit 163 so that both points are brought into coincidence with each other. The described operation is repeated to focus continuously. Thus, in this embodiment, the searching probe 154 significantly extends the measurable range, facilitating the coarse location of the calculus to be determined. The automatic tracking of the calculus greatly improves the efficiency of the fracturing operation.

In this embodiment, it is assumed that the center of gravity of a calculus, as determined by the processing of echo signals, represents the actual location of the calculus during the automatic tracking of the calculus. However, a fracturing operation may also be contemplated in which the size of a calculus is determined on the basis of the area of echo-throughs 150A, 150B (see FIG. 21), and the fracturing operation is continued until this area reduces below a given value. It is also possible to detect the size of the calculus by a treatment which removes the respective echo-throughs.

Figure 28:
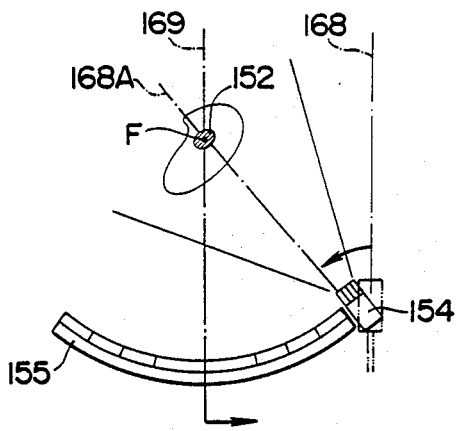
FIG. 28 is a schematic illustration of an apparatus according to a fifteenth embodiment of the invention.
Figure 29:
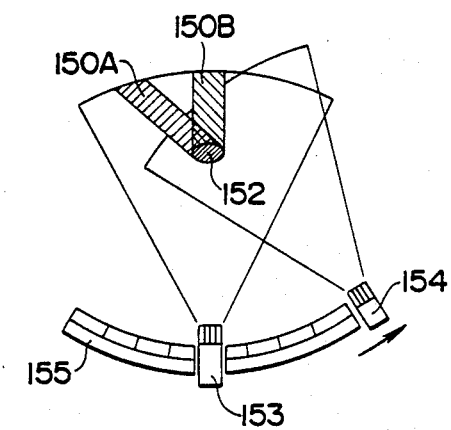
FIG. 29 is a diagram illustrating an echo-through which may occur in a tomographic image formed by an ultrasonic probe.

FIG. 28 is a schematic illustration of an apparatus according to a fifteenth embodiment of the invention, which is generally similar to the apparatus illustrated in FIG. 27 except that a searching probe 154 has an oscillatable axis 168 directed toward the center axis 169 on which the focus F of the ultrasonic wave generator 155 is located. The oscillation of the probe 154 enables it to oscillate in a direction indicated by an arrow in following relationship with the calculus 152 during the time the generator 155 is moved so as to bring the focus F thereof into coincidence with the calculus after the calculus 152 has been found on the axis 168A, thus maintaining its axis 168A in alignment with the calculus 152. After the generator has been focussed upon the calculus 152, the calculus 152 is automatically tracked on the basis of a tomographic image acquired by the probe 154. This embodiment has a simplified, smaller construction because it does not include the centrally located probe 153. FIG. 29 illustrates echo-throughs 150A, 150B caused by the calculus 152 in a tomographic image acquired by the probes 153, 154.

Figure 30:
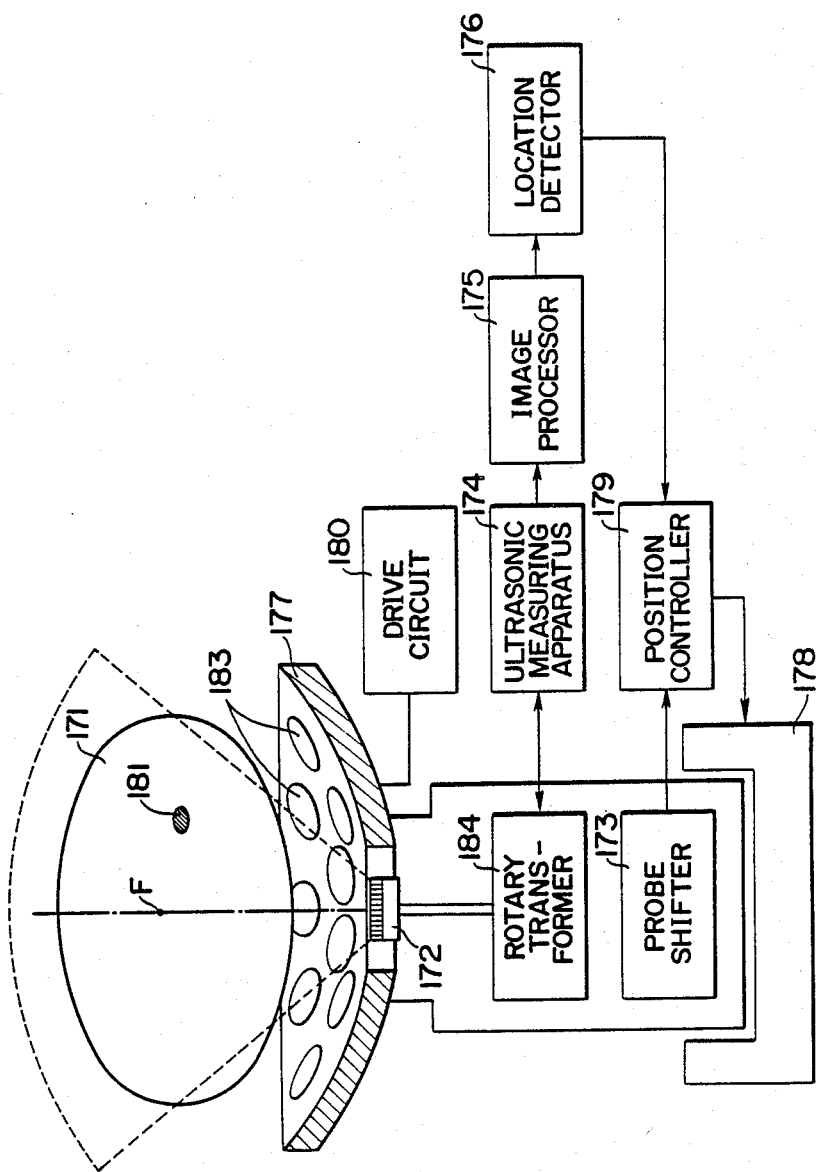
FIG. 30 is a schematic illustration of an apparatus according to a sixteenth embodiment of the invention.

FIG. 30 illustrates an ultrasonic therapeutical apparatus according to a sixteenth embodiment of the invention which is designed to provide a three-dimensional scan by an ultrasonic probe to acquire a plurality of two-dimensional tomographic images, representing sections of the physical body of a patient, which are then processed in real time to locate the calculus, positional information of which is utilized for focussing an ultrasonic wave.

In FIG. 30, an array 177 of ultrasonic vibrators or piezoelectric elements 183 disposed along a spherical surface in a mosaic pattern is driven by a drive circuit 180 to develop an ultrasonic wave of an increased intensity. The wave is focussed upon a focus F of the array 177. An ultrasonic probe 172 of electronic sector scan type derives a tomographic image of a sector-shaped area encompassed by broken lines.

The space between the patient 171 and the probe 172 is filled with a medium such as water to prevent attenuation of the ultrasonic wave. Alternatively, a bag filled with water, not shown, may be in close contact with the patient 171 while covering the array 177. The probe 172 is driven in an angular increment of 45°, for example, by an ultrasonic scanner 173 which may include a stepping motor, and at each angular position, an ultrasonic measuring apparatus 174 delivers an ultrasonic transmit pulse fed through a rotary transformer 184. An echo signal from the probe 172 is fed back to the measuring apparatus 174 through the transformer 184 to display a B-mode image. A video signal from the apparatus 174 is fed to an image processor 175, which cooperates with a location detector 176 to obtain information representing the location of a calculus 181, with such information being fed to a position controller 179. Information representing the angle of rotation of the stepping motor is supplied from the scanner 173 to the position controller 179, which then activates the array shifting unit 178 on the basis of such information.

Figure 31:
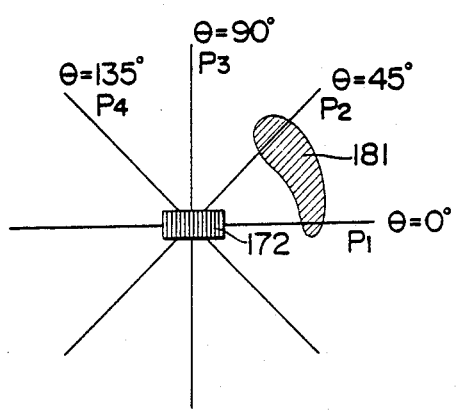
FIG. 31 is a diagram of an example of angle of rotation of an ultrasonic probe used in the apparatus of FIG. 30.
Figure 32:
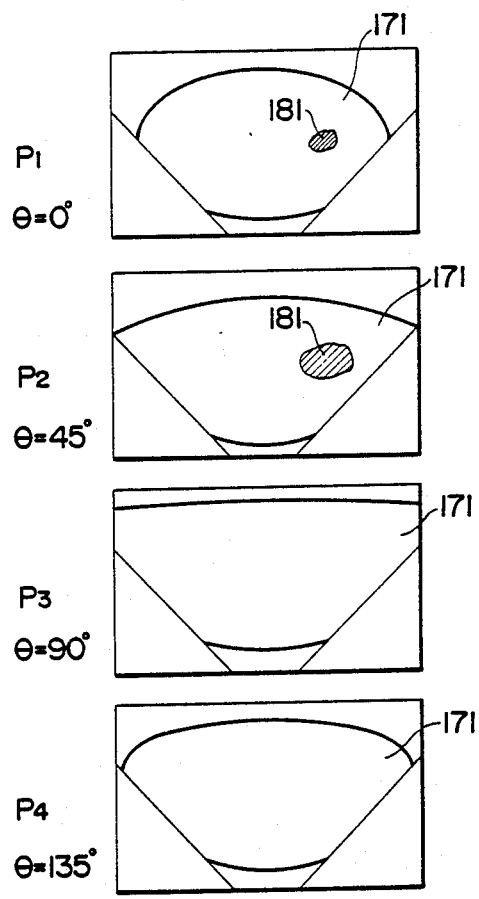
FIG. 32 illustrates several B-mode images at different angles of rotation of the probe.
Figure 33:
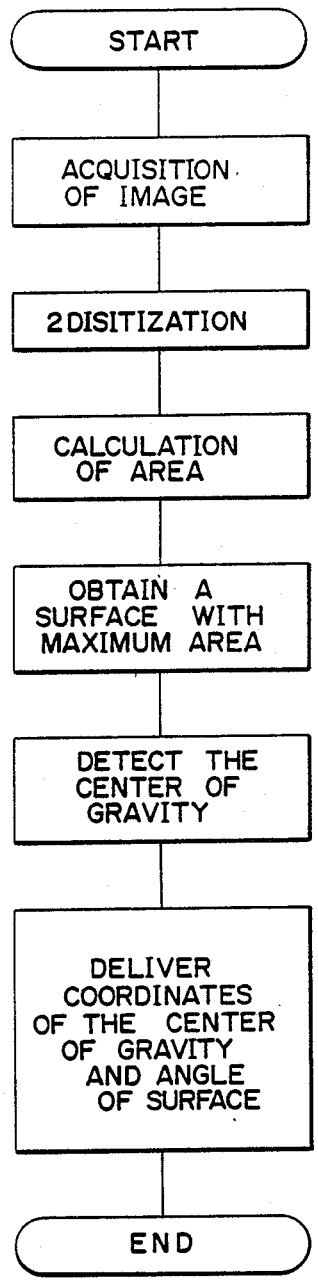
FIG. 33 is a flowchart illustrating a procedure which is utilized in the sixteenth embodiment to bring a calculus into the focal point of an array of vibrators.
Figure 34:
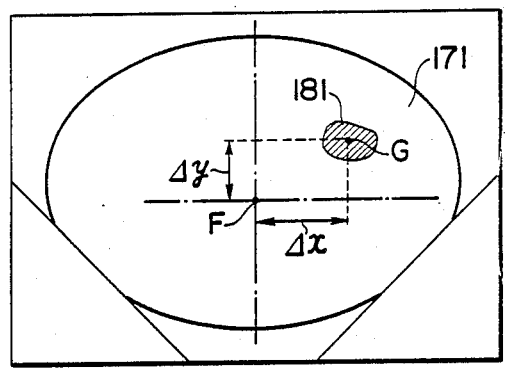
FIG. 34 illustrates a B-mode image, specifically illustrating the relationship between a calculus and the focal point of an array of ultrasonic vibrators on a P2 image plane illustrated in FIG. 32.

In operation, the probe scanner 173 rotates the probe 172 through angular increments to provide a B-mode image at each angular position which may correspond to an angular increment of 45°, for example, as illustrated in FIG. 31. By extracting areas of the image which exceed a given threshold in strength, four images P1 to P4 are obtained as indicated in FIG. 32. The combination of the image processor 175 and the location detector 176 operate upon each of these images P1 to P4 according to an algorithm indicated in FIG. 33. In this manner, information representing the B-mode image from the measuring apparatus 174 is acquired and stored in the image processor 175. Digitization may be performed to extract signal portions which exceed a given threshold, thereby facilitating the extraction of an echo which exhibits a greater strength than the remaining tissues. The echo area over such extracted portions of the calculus 181 is then calculated. One of the four images P1 to P4 which exhibits a greater area extracted for the calculus, which is the image P2 in the present example, is then determined. A corresponding angle of the scanner 173 (which is equal to 45° in this example) is determined. The location of the center of gravity G of the calculus represented by the echo in this plane is then determined (see FIG. 34), thus delivering the coordinates of the center of gravity G.

The location detector 176 then determines deviations $\Delta x$ and $\Delta y$ (see FIG. 34) of the center of gravity G from the focus F of the array 177 as well as the corresponding angle $\theta$ (see FIG. 34) of the probe scanner 173, delivering such information to the position controller 179. In response to information representing $\Delta x$, $\Delta y$ and $\theta$, the position controller 179 drives the array shifting unit 178 (which may include an X-Y-Z stage, for example) thus brining the focal point F of the array 177 into coincidence with the calculus 181 (see FIG. 30). Under this condition, the drive circuit 180 drives the array 177, causing the latter to emit an ultrasonic wave of an increased intensity concentrated upon the calculus situated at the focus F, thus fracturing it.

In the described embodiment, the B-mode image is acquired for each rotation of the probe through an angular increment of 45°, but the angular increment is not limited to this value. A smaller angular increment may be chosen to achieve a positional adjustment with a higher accuracy. For example, by driving the probe scan 173 at a rate of two revolutions per second and acquiring the image at an angular increment $\theta$ of 5°, thirty-eight B-mode images over an angular range of 360° may be processed within a time interval of 0.5 second, which is sufficient for tracking movement of the calculus for practical purposes. In this manner, the focus F of the ultrasonic wave is maintained at the center of gravity of the calculus which is represented by the echo, thus assuring maximum fracturing efficiency whenever the drive circuit 180 is energized.

Figure 35:
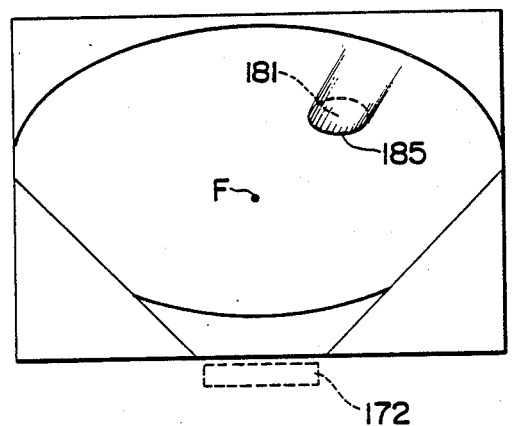
FIG. 35 shows a B-mode image, illustrating another use of the apparatus illustrated in FIG. 30.

FIG. 35 illustrates a mode image illustrating another use of the therapeutical apparatus illustrated in FIG. 30. It is assumed in the embodiment of FIG. 30 that the center of gravity of the echo representing a calculus coincides with the actual center of gravity of the calculus. However, with a calculus which exhibits an increased hardness, the nature of the ultrasonic wave may cause an echo 185 of an increased magnitude to be developed at the boundary of the calculus 181 located toward the probe 172 while failing to provide any echo for the remainder. In such a situation, a calculated location of the center of gravity of the echo may depart from the actual center of gravity of the calculus 181. To accommodate for this problem, the actual location of the calculus 181 may be inferred from a point nearest the probe 172 or from a configuration of the echo.

The probe 172 described above is an electronic sector type probe. However, a convex, linear or mechanical scan type probe may be used instead. Also, while the preferred embodiments have been described as systems for fracturing a calculus, the invention is also applicable to dissolution of thrombus, release of a progressively releasable agent (wherein an ultrasonic wave is externally irradiated upon a mass of material in which a medicine is impregnated to cause a progressive release of the latter), hypothermia or the like.

Figure 36:
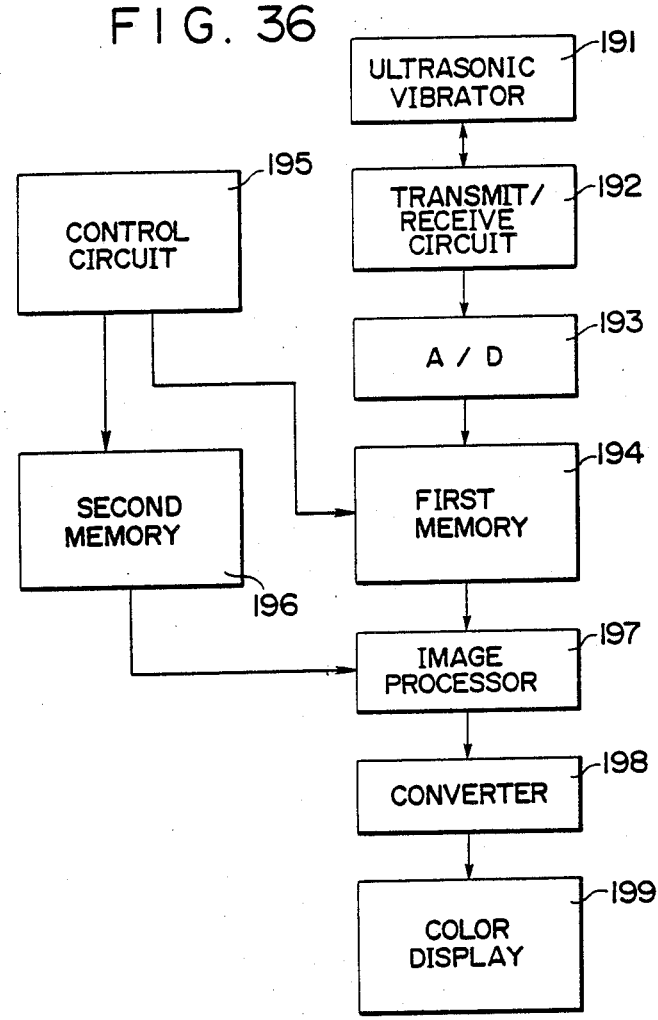
FIG. 36 is a block diagram of display means used in an apparatus according to a seventeenth embodiment of the invention.

FIG. 36 illustrates means for displaying an image obtained from an apparatus constructed according to a seventeenth embodiment of the invention and which is utilized to position a calculus into coincidence with a focal point of a fracturing shock wave. In this Figure, an ultrasonic vibrator 191 is driven by a transmit/receive circuit 192 to detect the spatial location of a calculus situated within the physical body of a patient. An ultrasonic echo signal received by the transmit/receive circuit 192 is fed through an A/D converter 193, where analog-to-digital conversion is made, to a first memory 194 which stores ultrasonic image data.

On the other hand, data representing the distribution of intensity of a shock wave from a shock wave generator, not shown, is previously calculated and stored in a second memory 196 which also defines an image memory. Both memories 194, 196 are controlled by a control circuit 195, which effects inputting image data from the respective memories into an image processor 197 where both data are synthesized. Specifically, based on the data representing the distribution of intensity of a shock wave supplied from the second memory 196, the image processor 197 allocates colors to the image depending on the intensity of the shock wave, and such color distribution signal is superimposed upon data representing an ultrasonic tomographic image supplied from the first memory 194. The superimposed signal is converted into standard television form by a standard television signal converter 198 before it is fed to a color display unit 199, which displays the resulting image.

Figure 37:
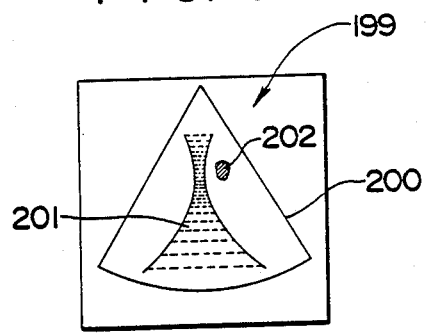
FIG. 37 is a diagram illustrating a data screen of the display.

FIG. 37 shows what is displayed on the screen of the color display unit 199. An ultrasonic tomographic image 200 and an image 201 representing the distribution of intensity of a shock wave are both superimposed upon each other on the screen. Since the image 201 is displayed in colors in superposition with the tomographic image 200 it is a simple matter to determine the location within the living body where the shock wave is applied and what the intensity of the shock wave is. This facilitates and assures that the calculus B is positioned at the point of maximum intensity of the shock wave. It is also easily determinable whether organs such as a lung, intestines or bones (which are sensitive to a shock wave) are close enough to risk damage, thus enabling any damage to these organs to be prevented.

In this embodiment, ultrasonic vibrators can be located at positions displaced 90° from each other so that the resulting tomographic images may be superimposed upon the distribution of intensity of the respective shock waves on the screen of the color display unit 199.

FIG. 38 illustrates another image display means in accordance with the invention. In this embodiment, coincidence of a calculus 202 with the point of maximum intensity of the shock wave is indicated by a change in the display within an image processor 197. FIG. 38 only illustrates the internal construction of the image processor 197, with the remaining construction being similar to that of FIG. 36. Specifically, tomographic data stored in a first memory 194 and data representing the distribution of intensity of a shock wave which is previously calculated and stored in a second memory 196 are fed to the image processor 197. Data representing the distribution of intensity of the shock wave is fed to a peak detector 203 where data having a maximum intensity is detected. An address corresponding to such data is fed to a control circuit 195 and then to a gate 204. Data representing a tomographic image supplied from the first memory 194 passes through the gate and an output of the data is fed to a comparator 205. Since the acoustical impedance of a calculus greatly deviates from the acoustical impedance of a living body, the calculus appears as an increased magnitude echo signal. A threshold of the comparator 105 is chosen whereby only the calculus is detected. When a signal exceeding the threshold or a picture signal of the calculus is supplied to the comparator 205, the color allocated to the tomographic image of the calculus is changed. An image processor 206 combines a signal representing the tomographic image from the first memory 194, an output from the comparator 205 and data representing the distribution of intensity of the shock wave (supplied from the second memory 196) together, and the combined signal is fed to a standard television signal converter 198 to permit it to be displayed on a color display unit 199. In this embodiment, when the calculus is positioned at a point of maximum intensity of the shock wave, a change in the color of the calculus occurs. This assures reliable positioning of the calculus.

Figure 39:
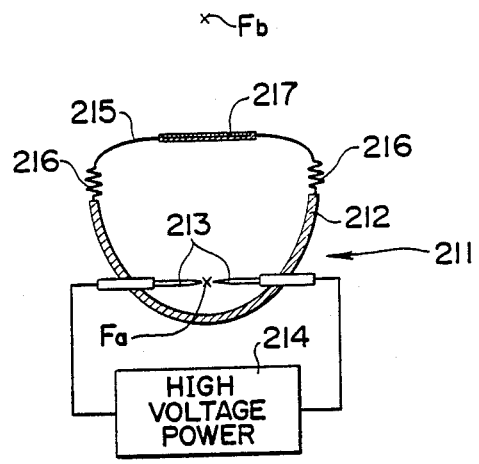
FIG. 39 is a longitudinal section through an ultrasonic probe and a shock wave generator which are used in an apparatus according to an eighteenth embodiment of the invention.
Figure 40:
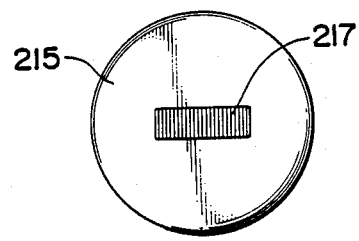
FIG. 40 is a plan view of the probe illustrated in FIG. 39.
Figure 41:
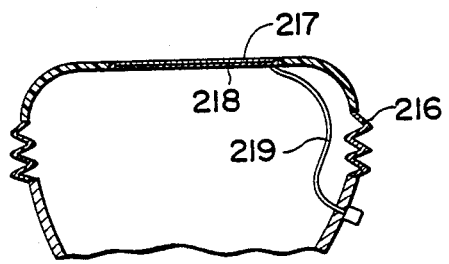
FIG. 41 is an enlarged, fragmentary longitudinal section of the probe illustrated in FIG. 39.

FIG. 39 illustrates an apparatus according to an eighteenth embodiment of the invention, specifically, an ultrasonic probe and a shock wave generator of an ultrasonic observation apparatus as well as a water bag in longitudinal section. FIG. 40 illustrates the generator and the water bag in plan view, and FIG. 41 is an enlarged longitudinal section of a top portion of FIG. 39. In this embodiment, a high tension discharge type shock wave generator is used to generate a shock wave to fracture a calculus. Specifically, the shock wave generator 211 includes a paraboloidal metal plate 212, high tension discharge electrodes 213 and a high tension source 214. A water bag 215 formed by a thin film is connected to the metal plate through bellows 216 which are connected to the upper edge of the metal plate 212, thus covering the top surface of the metal plate. An ultrasonic probe 217 with an array of ultrasonic vibrators is secured to the upper surface of the water bag 215 with a carrier member 218 (see FIG. 41) interposed therebetween. The probe 217 is connected through a lead wire 219 to a measuring apparatus, not shown. The discharge electrodes 213 are spaced apart, with the gap therebetween being centered about one of the foci, Fa, of the paraboloidal plate 212, and the shock wave is efficiently focussed upon the other focus Fb where a calculus or the like may be located.

The water bag 215 is made of GOATEX (trademark) which is permeable to a gas such as air, but which is impermeable to a liquid such as water. The bag 215 is internally filled with a shock wave transmitting medium such as water, and is deformable. The bag also includes means for injecting a liquid and means for controlling the pressure thereof. The probe 217 may be formed of a thin piezoelectric film of PVDV (polyvinylidene fluoride). It is supplied to the surface of the water bag 215 to effect a linear or a sector scan.

In operation, the surface of the water bag 215 is applied to the surface of the physical body of a patient in a region opposite to an affected area, and the probe 217 is utilized to scan the affected area to determine the location of a calculus or the like. Subsequently, the shock wave generator 211 is operated to bring the focus Fb of the paraboloidal plate 212 into coincidence with the calculus. A high tension discharge then takes place between the electrodes 213. Thereupon, a resulting shock wave is focussed upon the calculus located at the focus Fb, whereby the calculus is efficiently fractured.

Since the measuring unit is held in close contact with the patient, the distance to the affected area can be minimized to assure accurate measurement and to reliably detect the calculus. Where a piezoelectric film (such as the film mentioned above) is used, a high ultrasonic frequency can be used. This improves resolution relative to a probe with a conventional ceramic piezoelectric vibrator. This permits precise detection. The carrier member 218 (which supports the probe 217) may be simply placed on the surface of the water bag 215. Such a simple arrangement reduces cost.

Figure 42:
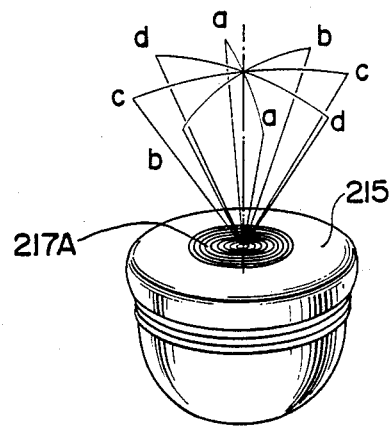
FIGS. 42 and 43 are a perspective view and a plan view of another form of probe.
Figure 43:
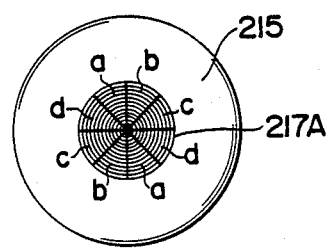
Figure 44:
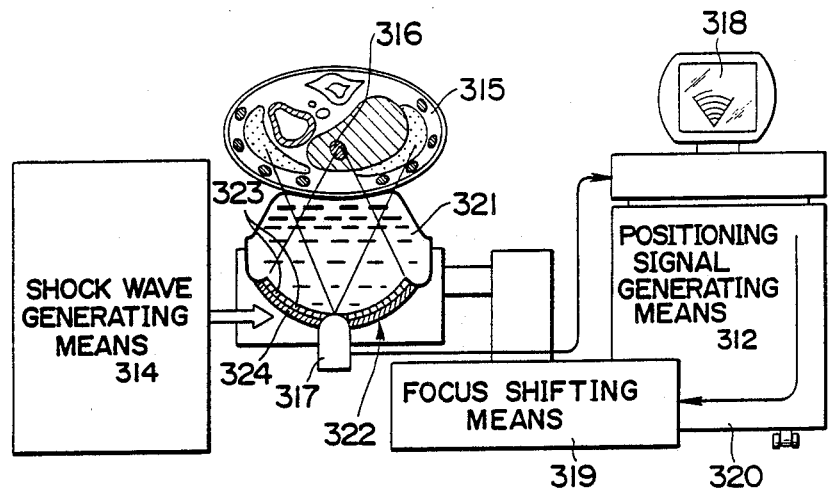
FIG. 44 is a schematic illustration of a conventional apparatus.
Figure 45:
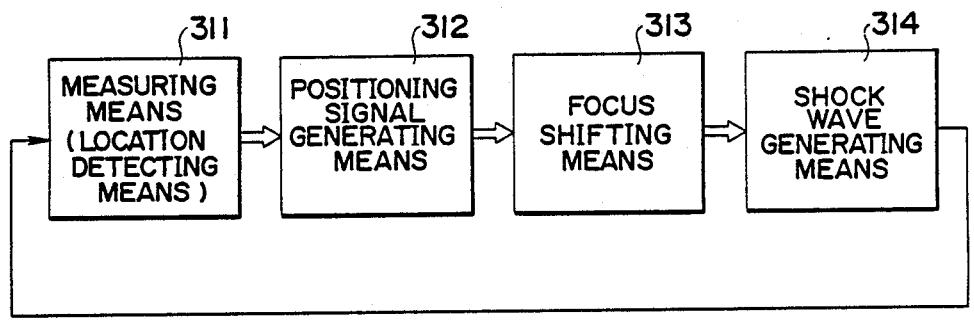
FIG. 45 is a block diagram illustrating the sequence of operation of the apparatus illustrated in FIG. 44.
Figure 46:
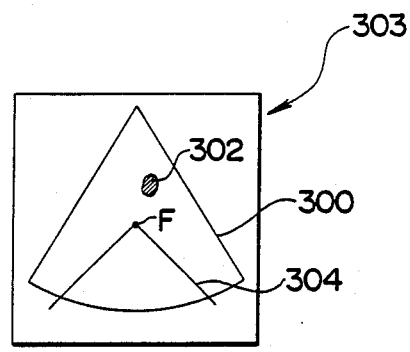
FIG. 46 is a diagram illustrating a conventional data display screen.

In the described embodiment, the probe 217 has a linear array, but other arrangements of ultrasonic vibrators may also be used as illustrated in FIGS. 42 and 43. Specifically, a piezoelectric film type ultrasonic probe 217A with piezoelectric elements disposed in concentric circles and a plurality of tomographic images may be obtained by scanning in different directions which represent an equal division of a circumference such as a—a, b—b, c—c and d—d directions. In this manner, the location of the calculus can be easily and accurately determined. The high tension discharge type ultrasonic generator in the described embodiment may be replaced by an ultrasonic shock wave generator with piezoelectric elements.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An extracorporeal therapeutic apparatus, comprising:
   locating means for locating the position of a target to be treated within a patient, said locating means generating and using ultrasonic waves;
   therapeutic energy generating means for generating and focussing therapeutic energy upon said target to be treated; and
   guiding and supporting means for movably guiding and supporting said locating means and said therapeutic energy generating means such that said locating means and said therapeutic energy generating means can be separately and independently guided to desired positions with respect to the surface of said patient, said guiding and supporting means being displaceable over said surface of said patient, wherein said guiding and supporting means includes: (a) a body which is movable toward and away from said patient; (b) a guide arm means for positioning said locating means at a desired angle for observation and for positioning said therapeutic energy generating means at a desired angle for efficient shock wave emission; (c) a head for supporting said guide arm means, said head being mounted on said body; and (d) means for rotating said head with respect to said body and for raising and lowering said head with respect to said body; and wherein said guide arm means includes a semicircular section and a horizontal support shaft, said support shaft being rotatably connected to said head such that said semicircular section can be positioned above and below said patient.

2. The apparatus of claim 1, wherein said locating means and said therapeutic energy generating means are slidably mounted on said semicircular section of said guide arm means.

* * * * *